(12) United States Patent
Himmelhaus

(10) Patent No.: US 8,471,217 B2
(45) Date of Patent: Jun. 25, 2013

(54) FLUORESCENT NON-METALLIC PARTICLES ENCAPSULATED IN A METALLIC COATING

(75) Inventor: Michael Himmelhaus, Tokyo (JP)

(73) Assignee: Fujirebio Inc., Tokyo (JP)

( * ) Notice: Subject to any disclaimer, the term of this patent is extended or adjusted under 35 U.S.C. 154(b) by 493 days.

(21) Appl. No.: 12/282,368

(22) PCT Filed: Apr. 26, 2007

(86) PCT No.: PCT/JP2007/059443
§ 371 (c)(1),
(2), (4) Date: Jan. 6, 2009

(87) PCT Pub. No.: WO2007/129682
PCT Pub. Date: Nov. 15, 2007

(65) Prior Publication Data
US 2009/0302235 A1    Dec. 10, 2009

Related U.S. Application Data

(60) Provisional application No. 60/796,162, filed on May 1, 2006.

(51) Int. Cl.
*G01N 21/64* (2006.01)
(52) U.S. Cl.
USPC ....................................... 250/458.1
(58) Field of Classification Search
USPC ....................................... 250/458.1
See application file for complete search history.

(56) References Cited

U.S. PATENT DOCUMENTS

| | | | |
|---|---|---|---|
| 5,759,767 A * | 6/1998 | Lakowicz et al. | 435/4 |
| 5,917,605 A * | 6/1999 | Colvin, Jr. | 356/417 |
| 6,699,724 B1 | 3/2004 | West et al. | |
| 2003/0174384 A1 | 9/2003 | Halas et al. | |

FOREIGN PATENT DOCUMENTS

| | | |
|---|---|---|
| EP | 0965835 A1 | 5/1999 |
| EP | 0965835 A1 | 12/1999 |
| WO | 01/06257 A1 | 1/2001 |
| WO | 03/093809 A1 | 11/2003 |

OTHER PUBLICATIONS

Becker et al. Optical stark effect in organic dyes probed with optical pulse of 6-fs duration, Physical Review Letters, vol. 60, No. 24 (Jun. 1998), pp. 2462-2464.*

(Continued)

*Primary Examiner* — David Porta
*Assistant Examiner* — Shun Lee
(74) *Attorney, Agent, or Firm* — Sughrue Mion, PLLC

(57) ABSTRACT

The present invention relates to a particle comprising a non-metallic core having a fluorescent material and a metallic shell encapsulating the non-metallic core wherein the metallic shell has transparency for an electromagnetic radiation having a first wavelength to excite the said fluorescent material and reflectance for an electromagnetic radiation having a second wavelength emitted by the said fluorescent material to confine the electromagnetic radiation having the second wavelength in the metallic shell. This system allows for the excitation of optical cavity modes inside the particle even at sub-micron particle size. The cavity modes are extremely sensitive to any change of the dielectric environment of the particle. This sensitivity can be used for the construction of optical nano-biosensors. Another application of the system is that of a microscopic source for spherical light waves, which may find applications in digital inline holography and display technology.

24 Claims, 18 Drawing Sheets

OTHER PUBLICATIONS

Enderlein Theoretical study of single molecule fluorescence in a metallic nanocavity, Applied Physics Letters, vol. 80, No. 2 (Jan. 2002), pp. 315-317.*

Astratov et al. Optical coupling and transport phenomena in chains of spherical dielectric microresonators with size disorder, Applied Physics Letters, vol. 85, No. 23 (Dec. 2004), pp. 5508-5510.*

Amarie et al. Submicrometer Cavity Surface Plasmon Sensors, Journal of Physical Chemistry B, vol. 109, No. 32 (Jul. 2005), pp. 15515-15519.*

Lakowicz et al. Plasmon-controlled fluorescence: a new detection technology, Proceedings of SPIE vol. 6099 (Jan. 2006), pp. 609909-1 to 609909-15.*

Andreani et al. Strong-coupling regime for quantum boxes in pillar microcavities: Theory, Physical Review B, vol. 60, No. 19 (Nov. 1999), pp. 13276-13279.*

Supplementary European Search Report corresponding to European Patent Application No. 07742878.7, dated Jun. 8, 2011.

Joseph R. Lakowicz, Plasmonics in Biology and Plasmon-Controlled-Fluorescence, vol. 1, No. 1, Mar. 22, 2006, pp. 5-33, XP002636946.

Jörg Enderlein, Theoretical Study of Single Molecule Fluorescence in a Metallic Nanocavity, Applied Physics Letter, vol. 80, No. 2, Jan. 14, 2002, pp. 315-317, XP012030920.

Jörg Enderlein, Spectral Properties of a Fluorescing Molecule Within a Spherical Metallic Nanocavity, Physical Chemistry Chemical Physics R. Soc. Chem. UK, vol. 4, No. 12, Jun. 15, 2002, pp. 2780-2786, XP002636943.

Kadir Aslan, et al., Plasmon Light Scattering in Biology and Medicine: New Sensing Approaches, Visions and Perspectives, Current Opinion in Chemical Biology, vol. 9, No. 5, Oct. 2005, pp. 538-544, XP002636947.

Kadir Aslan, et al., Metal-Enhanced Fluorescence Solution-Based Sensing Platform, Journal of Fluorescence Kluwer Academic/Plenum Publishers USA, vol. 14, No. 6, Nov. 2004, pp. 677-679, XP002636945.

Halas N., "Optical Properties of Nanoshells", Optics & Photonics News, vol. 13, Issue 8, pp. 26-30, Aug. 2002.

Himmelhaus M., et al., "Cap-shaped gold nanoparticles for an optical biosensor", Sensor & Actuators B 2000, 63, pp. 24-30.

Kuwata-Gonokami M., et al., "Laser Emission from Dye-Doped Polystyrene Microsphere", Japanese Journal of Applied Physics vol. 31, pp. L99-L101, Feb. 1, 1992.

Liu Y., et al., "Biosensing based upon molecular confinement in metallic nanocavity arrays", Nanotechnology col. 15, pp. 1368-1374, 2004.

Liu Y., S. Blair, "Biosensing based upon molecular confinement in mettalic nanocavity arrays", Proceedings of SPIE, vol. 5703, pp. 99-106, 2005.

Oldenburg S.J., et al., "Nanoengineering of optical resonances", Chemical Physics Letters vol. 288, pp. 243-247, May 22, 1998.

Painter et al., "Two-Dimensional Photonic Band-Gap Defect Mode Laser", Science vol. 284, pp. 1819-1821, Jun. 11, 1999.

Vahala, K. "Optical microcavities", California Institute of Technology, vol. 424, pp. 839-846, Aug. 14, 2003.

Vollmer et al., "Protein detection by optical shift of a resonant microcavity", Applied Physics Letters vol. 80, No. 21, pp. 4056-4059, May 27, 2002.

* cited by examiner (A)  (B)

(I)  (II)

FLUORESCENT NON-METALLIC PARTICLES ENCAPSULATED IN A METALLIC COATING

This application is a non-provisional application claiming a priority based on a prior U.S. Provisional Application No. 60/796,162 filed on May 1, 2006. The entire contents of the Provisional Application No. 60/796,162 and another prior U.S. Provisional Application No. 60/826,483 filed on Sep. 21, 2006 are incorporated herein by reference.

TECHNICAL FIELD

The present invention relates to an optical element comprising fluorescent non-metallic particle(s) with a metallic coating, a method for preparing said particle(s), an optical device comprising said particle(s) and an analytical method using said particle(s) which can be applied to the field of measuring or detecting small amounts of biological or chemical molecules.

BACKGROUND ART

Optical microcavities confine light to small volumes by resonant recirculation and have demonstrated potential use as microscopic light emitters, lasers, and sensors (K. J. Vahala, Nature Vol. 424, pp. 839-846, 2004). The recirculation imposes geometry-dependent boundary conditions on wavelength and propagation direction of the light kept inside the microcavity. Accordingly, only certain optical modes, the so-called "cavity modes", can be populated. Since the energy levels of these allowed modes depend crucially on geometry and optical properties of the microcavities, the latter comprise very sensitive microscopic optical sensors that can be used for example to sense forces (e.g. by deformation of the cavity) or changes in chemical concentration (e.g. by a corresponding change of the refractive index in close vicinity of the microcavity). Similarly, microcavities can be used for biomolecular detection, e.g. by surface adsorption of specifically binding molecules to or into a microcavity and the resultant change of the refractive index around or inside of the cavity.

The confinement of light inside of a microcavity requires a highly reflective boundary between the microcavity and surrounding. This can be achieved for example via total internal reflection, similarly to the guidance of light inside of an optical waveguide. As shown in FIG. 1, total internal reflection can occur if the refractive index of the microcavity, $n_{cav}$, is larger than that of its surrounding, $n_{env}$, i.e. $n_{cav} > n_{env}$. However, even in this case, total internal reflection occurs only for angles $\alpha$ above a so-called "critical angle" $\alpha_{crit} = \arcsin(n_{env}/n_{cav})$, where $\alpha$ is measured from the local surface normal inside of the cavity, where the reflection occurs. Such simple considerations remain valid as long as surface roughness is negligible as compared to the wavelength of the light trapped inside the microcavity. Accordingly, one general lower size limit of microcavities is given by the precision to which smooth surfaces can be prepared.

Another obstacle for utilization of microcavities is directly related to the requirement of a highly reflective interface between microcavity and surrounding. Since the path of light is reversible in absorption-free media, the interface will be also highly reflective for those light beams 20 that impinge onto the interface from the surrounding. Accordingly, just those optical modes inside the cavity, which fulfill the requirement of high reflectivity and thus provide long light storage potential, cannot be easily populated by light accessing the microcavity from the outside.

Vollmer and coworkers (F. Vollmer et al., Applied Physics Letters Vol. 80, pp. 4057-4059, 2002) used evanescent field coupling between the uncoated core of an optical fiber and a silica microsphere for population of the cavity modes inside of the microsphere. In this case, photons can transit from the high refractive index core of the fiber to the high refractive index interior of the microsphere via tunnelling through a small air gap. The air gap should be in the range of a few nanometers and has to be precisely controlled. For this reason, the microsphere has to be fixed to a solid mount, which in the case of Vollmer et al. also was used as microfluidic device for biosensing application. Vollmer et al. were able to demonstrate cavity mode biosensing via adsorption of bovine serum albumine (BSA) onto the outer surface of silica spheres with diameters of 300 μm. They showed that the sensitivity of their sensor scales with 1/R, where R is the particle radius.

Kuwata-Gonokami and coworkers (M. Kuwata-Gonokami et al., Japanese Journal of Applied Physics Vol. 31, pp. L99-L101, 1992) used dye-doped polystyrene (PS) microspheres for populating cavity modes. The dye-containing microspheres were radiated with ultrashort laser pulses to excite the dye molecules. The pump laser pulse was incident onto the microsphere surface at a small incidence angle $\alpha$, so that the light could penetrate into the optically denser microsphere with small loss only (~5-10%). The excited dye molecules inside of the microcavity re-radiate fluorescent light into arbitrary directions, i.e. also into those which fulfill the condition of total internal reflection. Accordingly, all cavity modes which fall into the emission wavelength range of the dye molecules became populated. At high pump intensities microcavity lasing was observed.

Halas and coworkers have suggested core-shell particles of much smaller size consisting of a non-metallic core and a metallic shell for optical biosensing (West et al., U.S. Pat. No. 6,699,724 B1). They studied in particular the size regime from few tens to several hundreds of nanometers, i.e. particles with an outer diameter of <1 μm. The conductive shell of such particles can be optically excited at the so-called "plasma frequency", which corresponds to a collective oscillation of the free electrons of the shell. While the plasma frequency of solid metal particles shows only marginal dependence on the particle size and is basically given by the physical properties of the bulk material, such as electron density and effective electron mass, Halas et al. were able to demonstrate that in the case of core-shell particles the position of the plasma frequency can be tuned over a wide range from the visible to the near infrared solely by changing the ratio between core and shell radii of the particles (N. Halas, Optics & Photonics News, Vol. 13, Iss. 8, pp. 26-31, 2002; S. J. Oldenburg et al., Chemical Physics Letters, Vol. 288, pp. 243-247, 1998). Halas et al. suggested to use such particles as biosensors by tuning the plasma frequency into a frequency range where it could support surface enhanced Raman emission of organic molecules adsorbed on the outer shell surface. The Raman emission then can serve as qualitative measure of protein adsorption. It must be noted, that Halas et al. use the core-shell character of the fabricated particles solely for tuning of the plasma frequency but not for generation or utilization of microcavity modes. In the course, they do not suggest to embed any kind of fluorescent material into the non-metallic particle cores for population of such modes.

Besides closed microcavities, also the utilization of open microcavities has been suggested for biosensing. These microcavities comprise microscopic vacancies in a thin metallic film. The light is confined only in the plane of the thin film, but free in perpendicular direction. Blair and coworkers (Y. Liu et al., Nanotechnology Vol. 15, pp. 1368-1374, 2004;

Y. Liu & S. Blair, Proceedings of SPIE Vol. 5703, pp. 99-106, 2005) studied fluorescent enhancement of dye-labeled proteins adsorbed into nanocavities patterned in a thin gold film. They observed fluorescent enhancement by a factor of 2 and an increase in quantum yield by a factor of 6. In contrast to what will be described below, there is no additional active medium, such as dye molecules or quantum dots for population of the cavity modes except those fluorophore labels attached to the analyte. Accordingly, the observed effects are rather weak and observable only with large scale assemblies of individual microcavities.

Scherrer and coworkers (O. Painter et al., Science Vol. 284, pp. 1819-1821, 1999) achieved the so far smallest microcavity volumes of 0.03 cubic micrometers with a single defect in a two-dimensional photonic crystal and confined light with a wavelength of 1.55 µm to it. In this calculation of the cavity volume, however, they did not include the overall size of the periodic structure that is required to keep the photons trapped. The latter will probably hamper the down sizing of sensors based on photonic crystals into the sub-micron regime.

There exist a variety of other methods for label-free biosensing based on plasma excitations of metal particles or thin metal films. In these cases, an incoming light wave is used to launch a free propagating or localized surface plasmon (which corresponds to a collective oscillation of the free electrons of the metal). The plasmon in turn produces an evanescent electromagnetic wave in the close environment of the metal film or metal particle. When the dielectric properties in this environment are altered, e.g. due to biomolecular adsorption, the plasmon oscillation alters its resonance position. Accordingly, this shift can be used as read-out signal of a label-free optical biosensor.

Examples of approaches utilizing localized plasmon effects are given in US 2003/0174384 A1, EP 0 965 835 A2 and Sensors and Actuators B 2000, 63, pp. 24-30. An example for utilization of free-travelling plasmons is given by the BIAcore system from Pharmacia Biosensor, Piscataway, N.J., USA. In none of these cases, however, microcavity modes have been suggested for amplification of said plasmon effects.

DISCLOSURE OF INVENTION

Summarizing, attempts of fabricating microcavities with sizes below one micron, i.e. "nanocavities", which might be useful for the development of true nanosensors, have not been successful so far. In the course of the inventors research, the main reasons for this lack of success were carefully investigated and were estimated as below:
(i) Non-metallic cavities without metallic coating, in which only so-called "Whispering Gallery Modes" (WGM) can be excited via total internal reflection, show a dramatic increase of losses with decreasing particle diameter, since the average incidence angle of the light onto the interface between particle and environment becomes smaller and smaller, thereby violating the condition of large incidence angles above the critical angle $\alpha_{crit}$. (ii) Further, surface roughness becomes more important for smaller particles, causing additional scattering of light into directions with low incidence angles $\alpha_i$ with the interface.

These problems were the recent subject matter of the inventor in his research and he conceived an invention that can circumvent the problems by the use of metallic coatings and fluorescent material embedded inside of a microcavity in combination with a means for exciting the fluorescent material as explained in detail below. Metallic coatings show a reflectance which is less dependent on the incidence angle of the light with the surface (cf. FIG. 1). However, exactly for this reason, a metallic coating shields the entire cavity from radiation impinging onto it from the outside. Therefore, excitation of a fluorescent material embedded inside of a microcavity for population of the cavity modes was not easy to achieve and therefore has not been tried by the others so far.

The present invention relates to a particle comprising a non-metallic core having a fluorescent material, and a metallic shell encapsulating the non-metallic core, wherein the metallic shell has transparency for an electromagnetic radiation having a first wavelength to excite the said fluorescent material and reflectance for an electromagnetic radiation having a second wavelength emitted by the said fluorescent material to confine the electromagnetic radiation having the second wavelength in the metallic shell. The said transparency can also be achieved by using a metallic shell which has small aperture(s) to enable the electromagnetic radiation to enter the non-metallic core. Such small aperture(s) of the metallic shell are located at the portion of the shell in contact with either a substrate or neighbouring particles, or otherwise the small apertures have a maximum area of $<\pi/4\lambda^2$, where $\lambda$ is the wavelength of the light intended to penetrate through the aperture.

In the said particle the non-metallic core may have one or more fluorescent material(s) selected from the group consisting of dye molecules, quantum dots, carbon nanotubes, Raman emitters an the like. The fluorescent material may be present either in the non-metallic core or on the surface of the non-metallic core. The non-metallic core may have the fluorescent material in the state of mixtures of said two or more fluorescent materials. The fluorescent material(s), which may be either a single species or a mixture of a plurality of species, can be distributed homogeneously or heterogeneously throughout the volume or the surface of the core.

The fluorescent material(s) can be arranged in an ordered or disordered fashion throughout the cavity core or its surface. In the particle encapsulated in a metallic coating, the cavity core can comprise a photonic crystal with the fluorescent material either arranged periodically or distributed randomly over the photonic crystal.

The fluorescent material used in the present invention can be excited by an electromagnetic radiation having a first range of wavelengths $\lambda_{exc}$ and can emit an electromagnetic radiation having a second range of wavelengths $\lambda_{em}$. The metal shell used in the present invention shows high reflectance at least within a part of the second range of wavelengths emitted by the fluorescent material. In addition, the emission wavelength of the fluorescent material may cover the spectral range of the surface plasmon resonance of the metallic shell.

One of the embodiments of the present invention can be described in relation to the particle encapsulated in a metallic coating, wherein the fluorescent material is excited by means of ultrashort laser pulses, which results in the population of the excited states that exceeds that of the ground state, i.e. a basic lasing condition is fulfilled at least temporally.

Further, the particle may be supported by a supporting substrate and small apertures in the metallic coating may exist only in contact to the supporting substrate. The said small apertures in the metallic coating may further exist in contact to neighbouring cavities in an assembly.

In the particle(s) of the present invention, the volume of the cavity core (V), the quality factor of the cavity core (Q), and the emission wavelength ($\lambda_{em}$) of the fluorescent material may be chosen such, that inside the cavity the relation satisfies the inequality (I):

$$1 < 3Q\lambda_{em}^3/4\pi V \tag{I}$$

The volume of the said cavity core may be $\leq 1000$ μm$^3$, more preferably $\leq 100$ μm$^3$, most preferably $\leq 1$ μm$^3$. The cavity volume ($V_{min}$) and at least a part of the emission wavelength range ($\lambda_{em}$) of the fluorescent material inside the cavity core may be selected so as to satisfy the condition (II):

$$V_{min} = f(\lambda_{em})^3, \tag{II}$$

and the factor f is $<5$, more preferably $<3$, and most preferably $<1$.

In the particle(s) of the present invention, the quality factor of the cavity may be $>1$, more preferably $>3$, even more preferably $>5$, even more preferably $>10$, most preferably $>50$.

Also, in the particle(s) of the present invention, at least a part of the emission range ($\lambda_{em}$) of the fluorescent material may be selected so as to hold the following condition:

$$\frac{\lambda_{em} d^2 Q^2}{n_{cav}^2 V} > \frac{\pi c \varepsilon_0 \hbar}{2} = 4.40 \times 10^{-37} Coulomb^2, \tag{III}$$

where d is the transition dipole moment of the fluorescent material corresponding to $\lambda_{em}$, $n_{cav}$ is the refractive index of the cavity core, Q its quality factor (with respect to $\lambda_{em}$) and V its volume.

A further aspect of the present invention relates to a coupled particle system containing at least two of the particles according to claim 1, wherein the particles are located in close contact with each other such that one or more of the cavity modes within the metallic shells couple with each other. The said coupled particle system may comprise particles which may be located in close contact with each other such that photons can tunnel from one cavity to a neighbouring one with a probability $>10^{-6}$. When the tunnelling probability is less than $10^{-6}$, it would be difficult to achieve coupling of sufficient strength for its observation. In the coupled particle system of the present invention, the particles may be located in close contact with each other such that the cavity modes of the cavities show a mode splitting due to the contact. Preferably in the coupled particle system of the present invention, the coupled emitter/cavity modes of cavities in contact with each other and which may be both (or all) in the strong coupling regime as described below show additional coupling due to the contact.

The other aspect of the present invention relates to a biosensor for sensing a target molecule which comprises the particle described above. Here the particle of the biosensor of the present invention comprises a non-metallic core having a fluorescent material; and a metallic shell encapsulating the non-metallic core; wherein the metallic shell has transparency for an electromagnetic radiation having a first range of wavelengths to excite the said fluorescent material and reflectance of an electromagnetic radiation having a second range of wavelengths emitted by the said fluorescent material to confine the electromagnetic radiation having the second wavelength in the metallic shell. The biosensor of the present invention comprises the said particle; a capturing molecule that is immobilized on an outer surface of the particle and is capable of capturing the target molecule; a means for emitting electromagnetic radiation having the first range of wavelengths; and a detector for detecting electromagnetic radiation around the second range of wavelengths, wherein the change in the electromagnetic radiation from the particle indicates the capture of the target molecule. In the biosensor for sensing a target molecule, the fluorescent material is excited via means of an external electromagnetic radiation, preferably a laser beam, most preferably an ultrashortpulse laser beam and the detection is performed via an optical system, such as a lens system, a fiber probe or waveguide. A high resolution microscopy system, a sharpened fiber tip 27 or other type of aperture with an opening below the diffraction limit may be preferably used in case of nano-scale sensors.

Furthermore, the present invention provides arrays or clusters of particles of the particles described above for use in signal amplification and/or built-in referencing. Arrays of surface adsorbed or embedded particles can be applied to the monitoring of their interference pattern, e.g. by means of a CCD camera. The interference pattern depends strongly on the condition of the individual particles, thus allowing parallel read-out of a multitude of particles. Arrays of surface adsorbed or embedded particles of the present invention also can be applied to a multiple ultrasmall light source for applications in display technology and related art.

The present invention also provides systems of freely floating particles, wherein the particles have a structure described above and are dispersed in a fluid that is transparent to the wavelengths of the electromagnetic radiation having a first range of wavelengths which excite the fluorescent material and the electromagnetic radiation having a second range of wavelengths emitted by the fluorescent material. The free floating particles of this system may contain more than one species of fluorescent materials for broader excitation of cavity modes. In this system, the fluorescent materials may be excited by more than one electromagnetic radiation.

The present invention further provides a single substrate-supported particle system, wherein the particles have a structure described above and are embedded in a matrix that is transparent to the wavelengths of the electromagnetic radiation having a first range of wavelengths which excite the fluorescent material and the electromagnetic radiation having a second range of wavelengths emitted by the fluorescent material. The single substrate-supported particles may contain more than one species of fluorescent materials for broader excitation of cavity modes.

An embodiment of the above freely floating particle system or the single substrate-supported particle system may be microscopic sources for spherical waves. Applications of such freely floating particle systems or the single substrate-supported particle systems can be for the use in digital in-line holography for in-situ and in-vivo observation of biological interactions and events. These systems will be explained later in more detail.

BRIEF DESCRIPTION OF DRAWINGS

FIG. 1(a) In the case of a non-metallic cavity, light can be trapped via total internal reflection for all incidence angles $\alpha_i$ above a so-called "critical angle" $\alpha_{crit}$, if the real part of the refractive index $n_{cav}$ of the cavity is larger than that of its environment $n_{env}$. Light impinging onto the surface at an angle $\alpha_i < \alpha_{crit}$ can easily transmit through the surface, thereby also allowing access of the cavity from the outside ("o"), as needed, e.g. for optical pumping of fluorescent material inside of the cavity. FIG. 1(b) In the case of a metal-coated cavity, light impinging onto the metal coating is reflected for arbitrary angles. This facilitates trapping of light inside of the cavity, but hinders optical access of the cavity from the outside, e.g. as needed for optical pumping of fluorescent material inside of the cavity.

FIG. 2(a): Metal-coated cavities: Due to the free charge carriers inside of a metal, the electric field at the inner surface of the metal coating has to vanish for all times. Accordingly, only those cavity modes can be excited, which have knots at the inner surface of the metal coating. From this condition, the cavity modes can be calculated as $\lambda_m = 4\ n_{cav} R/m$, where R is the inner radius of the cavity, $n_{cav}$ is its refractive index, and m is an integer. FIG. 2(b): Non-metallic cavities: Light can only be trapped for incidence angles with the inner cavity surface larger than the critical angle, which is smaller than 90 only if the refractive index of the cavity, $n_{cav}$, is larger than that of the environment $n_{env}$ (cf. FIG. 1). Due to this restriction, the integer m has to be chosen sufficiently high, typically m≈100. Then, light traveling along the circumference, $2\pi R$, of the sphere can be stored if it fulfils the condition for constructive interference $\lambda_m = 2\pi n_{cav} R/m$. Scaling down of these systems below one micron in diameter has not been achieved so far, since in such a case the average incidence angle decreases, thereby dropping below the critical angle. For both cases, a rigorous treatment using Maxwell's equations yields similar results for the radial dependence of the cavity modes, which is most important here.

BEST MODE FOR CARRYING OUT THE INVENTION

As it was described above, the present embodiment provides a particle 1 which is useful as an optical element for a small scale device such as a bionanosensor, a digital in-line holography system, and the like, which a particle 1 comprises a non-metallic core 2 having a fluorescent material 3; and a metallic shell 4 encapsulating the non-metallic core 2; wherein the metallic shell 4 has transparency for an electromagnetic radiation having a first range of wavelengths to excite the said fluorescent material 3 and reflectance of an electromagnetic radiation having a second range of wavelengths emitted by the said fluorescent material 3 to confine at least a part of the electromagnetic radiation having the second range of wavelengths in the metallic shell 4. In this specification the terms described below will be used in the meanings as specified, respectively.

Definition Of Terms

Reflection and transmission at a surface: In general, the surface of a material has the ability to reflect a fraction of impinging light back into its ambient, while another fraction is transmitted into the material, where it may be absorbed in the course of its travel. In the following we call the power ratio of reflected light to incident light the "Reflectivity" or "Reflectance", R, of the ambient/material interface. Accordingly, the power ratio of transmitted light to incident light is called the "Transmittance", T, of this interface. Note, that R and T both are properties of the interface, i.e. their values depend on the optical properties of both, the material AND its ambient. Further, they depend on the angle of incidence and the polarization of the light impinging onto this interface. R and T both can be calculated by means of the Fresnel equations for reflection and transmission. The term "absorption" is defined in Example 5.

Figure 1:
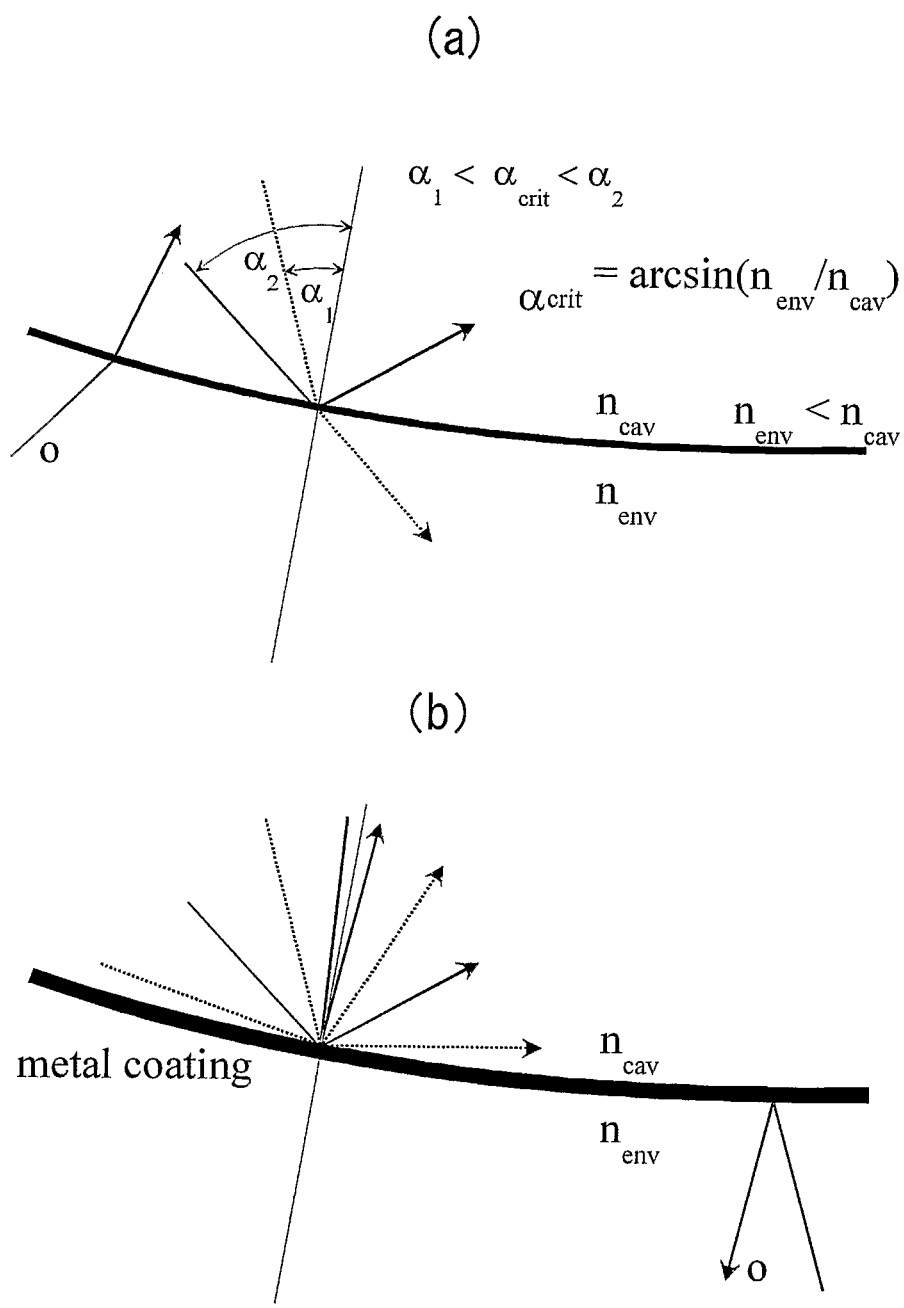
FIG. 1: Examples for potential reflective properties of cavity surfaces.

Optical cavity: An optical cavity is a closed volume confined by a closed boundary area (the "surface" of the cavity), which is highly reflective to light in the ultraviolet (UV), visible (vis) or infrared (IR) region of the electromagnetic spectrum. Besides its wavelength dependence, the reflectance of this boundary area may also be dependent on the incidence angle of the light impinging on the boundary area with respect to the local surface normal (cf. FIG. 1). The inner volume of the optical cavity may consist of vacuum, air, or any material that shows high transmission in the UV, vis, or IR. In particular, transmission should be high at least for a part of those regions of the electromagnetic spectrum, for which the surface of the cavity shows high reflectance.

An optical cavity is characterized by two parameters: First, its volume V, and second, its quality factor Q. In the following, the term "optical cavity" refers to those optical cavities with a quality factor Q>1.

Volume of an optical cavity: The volume of an optical cavity is defined as its inner geometrical volume, which is confined by the surface of the cavity, i.e. the highly reflective boundary area.

Quality factor: The quality factor (or Q-factor) of an optical cavity is a measure of its potential to trap photons inside of the cavity. It is defined as $$Q = \frac{\text{stored energy}}{\text{loss per roundtrip}} = \frac{\omega_m}{\Delta \omega_m} = \frac{\lambda_m}{\Delta \lambda_m}, \qquad (1)$$

where $\omega_m$ and $\lambda_m$ are frequency and wavelength of cavity mode m, respectively, and $\Delta\omega_m$ and $\Delta\lambda_m$ are the corresponding linewidths. The latter two equations connect the Q-factor with position and linewidth of the optical modes inside of the cavity. Obviously, the storage potential of a cavity depends on the reflectance of its surface. Accordingly, the Q-factor is wavelength dependent.

Optical cavity mode: An optical cavity mode or just "cavity mode" is a wave solution of the electromagnetic field equations (Maxwell equations) for a given cavity. These modes are discrete and can be numbered with an integer m due to the restrictive boundary conditions at the cavity surface. Accordingly, the electromagnetic spectrum in presence of the cavity can be divided into allowed and forbidden zones. The entire solution of the Maxwell equations consists of internal and external electromagnetic fields inside and outside of the cavity, respectively. In the following, the term "cavity mode" refers to the inner electromagnetic fields inside the cavity unless otherwise stated. The wave solution depends on the shape and volume of the cavity as well as on the reflectance of the boundary area, i.e. the cavity surface. Therefore, the solutions depend on the Q-factor of the cavity and its wavelength dependence.

Figure 2:
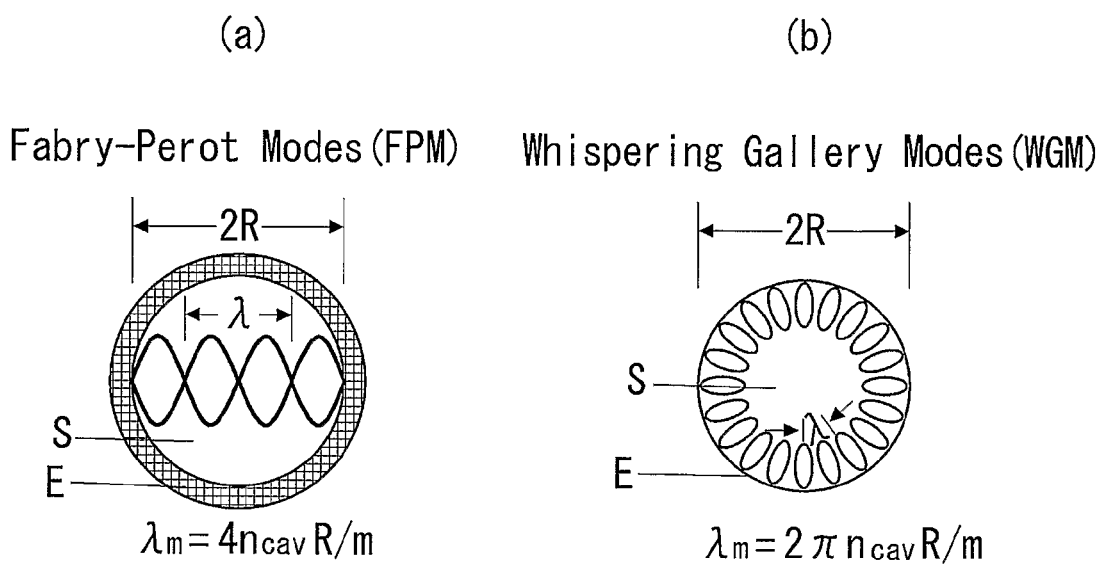
FIG. 2: Simplifying estimation for the cavity modes of microcavities.

For spherical cavities, there exist two main types of solutions, for which the wavelength dependence can be easily estimated. For simplicity, we will use these estimates in the discussion below. FIG. 2 illustrates the difference between the two solutions. In both cases, a standing wave has formed. FIG. 2(a) shows the standing wave formed in radial direction, while FIG. 2(b) shows the standing wave formed along the circumference of the inner boundary between sphere S and environment E (in the case of a sphere S coated with a conductive shell, the standing wave forms at the inner shell boundary).

In the following, we will call the radial modes "Fabry-Perot Modes" (FPM) due to analogy with Fabry-Perot interferometers. The modes forming along the circumference of the spheres S are called "Whispering Gallery Modes" (WGM) in analogy to an acoustic phenomenon Lord Rayleigh discovered more than a hundred years ago in the dome of St. Paul's cathedral in London. For a simple mathematical description of the wavelength dependence of these modes, we use the standing wave boundary conditions in the following (for illustration, cf. FIG. 2):

$$\lambda_m = 4Rn_{cav}/m, \; m=1, 2, 3, \qquad (2)$$

for FPM and $$\lambda_m = 2Rn_{cav}/m. \qquad (3)$$

for WGM, respectively. Here, "m" is an integer and also used for numbering of the modes, R is the sphere radius, and $n_{cav}$ the refractive index inside of the cavity.

Mode volume of a cavity mode: The mode volume of a cavity mode is defined as that geometrical volume, where the field intensity of the mode is not vanishing. Since in general the fields are decaying exponentially, a certain cut-off value defining "zero intensity" has to be set in practise. For example, the cut-off can be fixed to 0.1% of the maximum field intensity.

Optical Coupling between Cavities: According to our definition of small tolerable apertures in the metallic shell (cf. page 29), we define "optical coupling" between two adjacent cavities in a way that the light intensity getting from one cavity to the other is higher than what we expect for the accidental case, that two apertures, each in one of the metallic shells of the two cavities, respectively, come into contact with each other, thereby causing light to transit from one cavity into the other.

According to the Bethe limit, the transmittance $T_{ph}$ through a small aperture scales with its radius r as $$T_{ph} = \left(\frac{r}{\lambda}\right)^4 T_{ph,0},$$

where $$T_{ph,0} = \frac{A_{ph}}{4\pi R^2}$$

is the nominal transmittance through an aperture of area $A_{ph}$ located on a cavity of radius R. In the materials section, we defined the maximum allowable area of a small aperture in the metallic shell 4 as $$A_{ph} = \frac{\pi}{4}\lambda^2.$$

From the latter equation a maximum acceptable aperture radius of $r_{max}=\lambda/2$ results, which gives a maximum tolerable transmission through the small aperture of $$T_{ph,max} \propto \left(\frac{r_{max}}{2r_{max}}\right)^4 T_{ph,0} = \frac{1}{16} T_{ph,0}.$$

Now, if two small apertures, each located on one of the neighboring cavities, respectively, are in direct contact with each other, the maximum total transmission from one cavity into the other is given by $$T_{tot} = T_{ph,max}^2 \propto \frac{1}{256} T_{ph,0}^2.$$

On this basis, we define the term "cavities in optical contact with each other" such that the intensity of light passing from one cavity to the other, $T_{coupl}$, is larger than $T_{tot}$. Since only one half space of a given cavity can emit light into the direction of the other cavity, we introduce an additional factor ½, thus yielding $$T_{coupl} > \frac{1}{2} T_{tot} = \frac{1}{2} T_{ph,max}^2 \propto \frac{1}{512} T_{ph,0}^2.$$

Re-substituting the definition of $T_{ph,0}$ finally gives $$T_{coupl} > \frac{1}{512}\left(\frac{\lambda^2}{16R^2}\right)^2 \approx 7.6 \cdot 10^{-6}\left(\frac{\lambda}{R}\right)^4.$$

For a given wavelength, the smallest possible radius R of the cavity is—according to eq. 2 (with m=1):

$$R = \frac{\lambda}{4},$$

if we assume a refractive index of the cavity of $n_{cav}=1$. Therefore, altogether, we achieve at a save upper limit for the minimum transmittance between two particles in optical contact with each other $$T_{coupl} > \frac{1}{512}\left(\frac{\lambda^2}{16R^2}\right)^2 \frac{1}{512}\left(\frac{\lambda^2}{\lambda^2}\right)^2 \approx 2 \cdot 10^{-3}.$$

This definition can be easily extended to coupling of more than two cavities by considering all possible pairings the ensemble exhibits and applying above criterion for each pair.

Observable Quantum Effect

The present embodiment provides a particle 1 comprising a non-metallic core 2 having a fluorescent material 3 and a metallic shell 4 encapsulating the non-metallic core 2, the use of such a particle 1 in a small scale device as well as a way of fabricating closed metal cavities for the said particle 1, in which optical cavity modes can be excited from the outside without suffering from the high reflection losses for the external pump radiation as usually found in such systems. Therefore, a high population of the cavity modes can be achieved by the present embodiment. Due to the optical properties of the metallic coating 4, the cavities can be scaled down into the sub-micron size regime to form true "nanocavities". At such small size and high mode population, quantum effects become important in these systems, which are hardly observable in larger cavities with an average size above one micron. First of all, the small particle diameter causes a strong dependence of the position of the cavity modes on molecular adsorption, which can be used for the development of ultimate "single-molecule" nano-biosensors. Second, due to Purcell enhancement of the spontaneous emission rate of the fluorescent material 3 used for mode population inside of the nanocavity, the total radiative power of such nanocavities becomes significantly enhanced (factor of 30 or more), so that the cavity modes can be easily detected despite the small size of the nanocavity and stay well above the noise level. Finally, for very small cavities and very high cavity mode populations, further quantum effects, such as cavity mode splitting become observable. The dependence of this mode splitting on the refractive index in close vicinity of the nanocavity can be used for sensing applications, similar to the tracking of absolute cavity mode positions.

Figure 3:
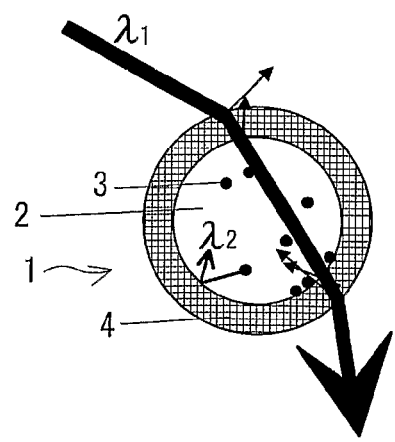
FIG. 3: Novel approach for fabricating small cavities for optical quantum confinement and nano-biosensing. A non-metallic particle that contains a fluorescent material, such as dye molecules, semiconductor quantum dots, carbon nanotubes, Raman emitters and the like, is coated with a metallic shell. The shell is highly transparent at the excitation wavelength $\lambda_1$ of the fluorescent material, however highly reflective in at least a part of its emission wavelength range $\lambda_2$. Therefore, the photons emitted by the fluorescent material due to fluorescence within that particular part of the emission wavelength range are trapped inside of the cavity.

A cavity with the ability to confine photons, if they match the frequency of a given cavity mode m, can be fabricated in the following way:

A small non-metallic particle having a fluorescent material 3, such as dye molecules, semiconductor quantum dots, carbon nanotubes, Raman emitters or the like inside or on the surface thereof, is coated with a metallic shell 4, e.g. made from silver (FIG. 3). Here, the metallic shell 4 functions as the "highly reflective closed boundary area" as introduced in the above definition. The fluorescent material 3 inside or on the surface of the core 2 of the particle 1 is excited by means of a pump laser or another strong light source operating at a wavelength that can easily penetrate the metallic coating 4. In the case of a silver shell for example, the wavelength can be chosen to be located around 320 nm, since silver shows maximum transmission around this value. The fluorescent material 3 is chosen such that it emits at a wavelength for which the metallic coating 4 shows high reflectance. Accordingly, the emitted photons are trapped inside of the cavity and the latter confines the photons to a small volume. In accordance with the present embodiment, the following quantum effects will be observable principally in such systems depending on volume and Q-factor, which can all well be utilized for optical sensing on the nanoscale:

1. Quantum Interference

The cavity modes depend on the geometry (volume and shape) of the cavity as well as the reflectance of its surface, which actually defines the Q-factor of the cavity. In the case of photons inside of a spherical metal-coated cavity, the allowed wavelengths of the cavity modes can be described in good approximation by eq. 2. This simplified equation is deduced from the fact that the field intensity has to vanish on the metal coating 4 at any time (FIG. 2). The exact position of the cavity modes depends crucially on the size of the spherical cavity. A simple calculation yields $$\frac{\Delta\omega_m}{\omega_m} = \frac{\Delta\lambda_m}{\lambda_m} = \frac{\Delta R}{R}. \quad (4)$$

Due to its 1/R dependence, the sensitivity due to changes in R, e.g. as caused by adsorption of biomolecules at the outer surface of the particles 1, increases with decreasing particle diameter. At the same time, the surface of the particles 1 decreases as $1/R^2$, so that less and less biomolecules adsorbed on the outer surface of the particles 1 are required to yield an increasing shift. At the nanoscale, where R is in the range of some tens to some hundreds of nanometers, sensitivity to such biomolecular adsorption should reach a maximum. The limit is given only by the minimum volume $V_{min}$ of the cavity into which a photon of wavelength λ can be squeezed. According to Eli Yablonovitch, Caltech, $V_{min}$ is given by $$V_{min} = 0.25\left(\frac{\lambda}{n_{cav}}\right)^3, \quad (5a)$$

where $n_{cav}$ is the refractive index inside of the cavity (E. Yablonovitch, "Photonic Bandgap engineering", Interim Progress Report, period 1/1-12/31/1998, U.S. Army Research Office, DAAH 04-96-1-0389, approved for public release). On basis of eq. 5a, a simple calculation can be performed to show the sensitivity of nano-biosensors utilizing cavity modes (cf. example 1). λ denotes the vacuum wavelength, so that $\lambda/n_{cav}$ is simply the wavelength of the photon inside of the cavity. In practice, it is difficult to achieve the limit as given by eq. 5a. Therefore, we write eq. 5a more generally in the form $$V_{min} = f\left(\frac{\lambda}{n_{cav}}\right)^3, \quad (5b)$$

where $f \geq 0.25$. The factor f then serves as a measure, how close an experimental approach has reached the theoretical limit. State-of-the-art experiments with whispering gallery modes in dye-doped polystyrene beads, for example, have accomplished values of only down to f≈135. The lowest f values have been so far obtained in photonic crystal structures, if only the mode volume is taken into account instead of the entire photonic crystal. Then, f=1.2 has been achieved (K. J. Vahala, Nature Vol. 424, pp. 839-846, 2004).

2. Purcell Enhancement

In addition to high sensitivity, the radiative power of the system has to be sufficiently high to allow for detection of binding events. The radiative power in nanocavities can be enhanced due to another quantum effect, the so-called "Purcell enhancement". In 1946 Edward M. Purcell stated in his work on spontaneous emission probabilities at radio frequencies that a dipole emitter coupled to a resonator would show an increased spontaneous emission, if the position of its emission frequency matches the resonance. Accordingly, for dipole emitters operating at optical frequencies, the rate of spontaneous emission, $\gamma_{SE}$, is given by $$\gamma_{SE} = \frac{2}{\varepsilon_0 \hbar}\left(\frac{d}{n_{cav}}\right)^2 \frac{Q}{V}, \quad (6)$$

if the emitter is placed inside of an optical cavity. Here, d is the dipole moment of the dipole emitter, $n_{cav}$ the refractive index inside the cavity, V its volume, and Q its quality factor. $\varepsilon_0$ is the dielectric constant and $\hbar$=h/2π with Planck's constant h. The ratio between $\gamma_{SE}$ inside the cavity and the spontaneous emission rate of a free emitter, $\gamma_0$, is called "Purcell factor" $n_{cav}$ (=$\gamma_{SE}/\gamma_0$) and is given as $$\eta_{cav} = 3Q\left(\frac{\lambda_{em}}{n_{cav}}\right)^3 \Big/ 4\pi V, \quad (7a)$$

where $\lambda_{em}$ is the emission wavelength of the emitter. The spontaneous emission rate inside of a cavity increases with increasing quality factor Q and decreasing cavity volume V. For a simple estimate, cf. example 2. According to eq. 7a, the spontaneous emission inside of a cavity exceeds that of a free emitter if $$1 < 3Q\left(\frac{\lambda_{em}}{n_{cav}}\right)^3 \Big/ 4\pi V. \quad (7b)$$

3. Emitter-Cavity Coupling

For nanocavities close to the size limit as given by eq. 5a an additional quantum effect comes into play: the coupling between dipole emitters and cavity modes (see, for example, Andreani et al., Physical Review B, Vol. 60, pp. 13276-13279). If the emission frequency of the emitter matches one of the cavity modes, $\lambda_{em} = \lambda_m$, a mode splitting can occur, which can be written as $$\omega_\pm = \omega_0 - \frac{i}{4}(\Delta\omega_{em} + \Delta\omega_m) \pm \sqrt{g^2 - \left(\frac{\Delta\omega_{em} - \Delta\omega_m}{4}\right)^2}. \quad (8)$$

Thereby, $\Delta\omega_{em}$ and $\Delta\omega_m$ denote the linewidths of emitter and cavity mode, respectively. g is the so-called "coupling constant" and is given by $$g = \sqrt{\frac{\pi c d^2}{2\varepsilon_r \varepsilon_0 \hbar \lambda_{em} V}}. \quad (9)$$

Here, c is the vacuum speed of light and $\varepsilon_r$ is the dielectric function of the cavity material, for which the Maxwell relation, $\varepsilon_r = n_{cav}^2$, holds. All other symbols are as defined above. According to eq. 8, the maximum mode splitting $\Delta\omega_\pm$ is observed for $\Delta\omega_{em} = \Delta\omega_m$ and amounts to $\Delta\omega_\pm = 2$ g. This calculation is valid for a single emitter inside of the cavity. If there are N emitters present, the splitting increases with $N^{0.5}$. For sensor applications, changes in the mode splitting can be traced as a function of changes of the particle radius R, as discussed previously. The dependence of g on R is given by $$\frac{\partial g}{\partial R} = -\frac{3}{2}\frac{g}{R}. \quad (10)$$

Therefore, as already observed in the above section 1 (Quantum interference), sensitivity increases with decreasing cavity size. For a simple estimate on the expected sensitivity of a nano-biosensor based on this effect, cf. example 3.

Equation 8 indicates that the mode splitting occurs only if the inequality $$g > \left|\frac{\Delta\omega_{em} - \Delta\omega_m}{4}\right| \qquad (11)$$

is fulfilled. Further, to make the splitting experimentally observable, 2 g should exceed the linewidth of the resonances $\omega_\pm$, i.e.

$$g > \frac{\Delta\omega_{em} + \Delta\omega_m}{4}. \qquad (12)$$

To obtain a safe lower limit for the onset of emitter-cavity coupling for a given cavity, we assume $$\Delta\omega_{em} \ll \Delta\omega_m, \qquad (13)$$

which can be fulfilled by choosing a proper emitter. Then, ineqs. 11 and 12 both reduce to $$g > \frac{\Delta\omega_m}{4}. \qquad (14)$$

Insertion of eqs. 1 and 9 into ineq. 14 and use of $\lambda_{em} = \lambda_m$ finally yields a condition for the emitter and cavity parameters to allow for an experimentally observable mode splitting, i.e. emitter-cavity coupling $$\frac{\lambda_{em} d^2 Q^2}{n_{cav}^2 V} > \frac{\pi c \varepsilon_0 \hbar}{2} = 4.40 \times 10^{-37} \; Coulomb^2. \qquad (15)$$

Example 4 gives an estimate of this condition for a metal-coated polystyrene sphere.

4. Coupling Between Emitter and Surface Plasmons of the Metallic Shell

Plasmons are collective oscillations of the free electrons of a metal and for bulk oscillations, the "plasma frequency" is in a simple description given by $$\omega_p^2 = \frac{ne^2}{\varepsilon_0 m}, \qquad (16)$$

where n is the free electron density, e the electron charge, and m its mass.

Besides such bulk excitations, plasmons also can be generated along surfaces (surface plasmons, sp, cf. for example H. Raether, *Surface Plasmons on Smooth and Rough Surfaces and on Gratings*, Springer Verlag Berlin, 1988) and in small metallic particles (localized surface plasmons, lsp, cf. for example U. Kreibig and M. Vollmer, *Optical Properties of Metal Clusters*, Springer-Verlag, Berlin, 1995). For surface plasmons, at the vacuum/metal interface, the excitation frequency is $$\omega_{sp} = \frac{\omega_p}{\sqrt{2}}, \qquad (17)$$

while for plasmons confined to a bulk nanoparticle the excitation frequency is given by $$\omega_{lsp} = \frac{\omega_p}{\sqrt{1 + 2\varepsilon_{env}}}, \qquad (18)$$

where $\varepsilon_{env}$ is the dielectric constant of the particle's environment.

For gold nanoparticles with diameters in the range of some to some tens of nanometers, the plasmon resonance is typically found between 510 and 550 nm, depending on the particle size. Recently, Halas and coworkers demonstrated that for core-shell particles the position of the plasmon excitation of the metallic shell 4 depends solely on the core-to-shell ratio of the particles 1 and can be tuned over a wide range from the visible into the NIR region of the electromagnetic spectrum (N. Halas, Optics & Photonics News, Vol. 13, Iss. 8, pp. 26-31, 2002; S. J. Oldenburg et al., Chemical Physics Letters, Vol. 288, pp. 243-247, 1998). Therefore, a fluorescent material 3 or—alternatively—the core-to-shell ratio of the particles 1—can be easily chosen such that the emission wavelength of the fluorescent material 3 matches the excitation of the localized surface plasmons of the particles 1, i.e. the confining cavity. In such a case, the surface plasmons can be excited internally, i.e. from the inner volume of the cavity, instead of excitation with light impinging onto the core-shell particles from outside, as for example described in (West et al., U.S. Pat. No. 6,699,724 B1). Demonstrations of such novel art and its application to optical sensing are given in Examples 10 and 11 of the present invention.

For small cavities, a coupling between emitters, cavity, and surface plasmons of the metallic shell 4 is expected. This is of great interest for biosensing, since the exact position of the surface plasmon resonance is well known to depend very sensitively on the refractive index of its intimate environment (cf. eq. 18). This dependence is already used in several optical biosensors (US 2003/0174384 A1, EP 0 965 835 A2 and Sensors and Actuators B 2000, 63, pp. 24-30, G. Bauer et al., Mikrochimica Acta, Vol. 131, pp. 107-114, 1999). Here however, the signal-to-noise ratio is expected to be further increased due to quantum effects such as Purcell enhancement, which yield a stronger excitation of the localized surface plasmons as compared to state-of-the-art techniques.

Materials and Resources to be Used

The particles 1 of the present embodiment can be manufactured by using materials which are available to the public. The following explanations of the materials are provided to help those skilled in the art construct the particles 1 in line with the description of the present specification.

Cavity material: Materials that can be chosen for fabrication of the core 2 are those who exhibit low or substantially no electric conductivity and low absorption in that part of the electromagnetic spectrum, in which the cavity shall be operated. In practise, this is a region of the emission spectrum of the fluorescent material 3 chosen for excitation of the cavity modes. In contrast to excitation of whispering gallery modes as already used in the literature for biosensing (F. Vollmer et al., Applied Physics Letters Vol. 80, pp. 4057-4059, 2002) the material may scatter light. Further, there is no restriction on the real part of the refractive index of the core material, i.e. there is no need for a refractive index higher than the surrounding of the cavity. The reason for these differences to systems based on WGM is the metallic coating of the cavity, which reflects light independent of the refractive index of the core material at arbitrary incidence angles. Therefore, a wider range of materials can be chosen as compared to state-of-the-art techniques. For example, it is possible to choose a photonic crystal as the core material and to coat either the outer surface of the crystal with a fluorescent material 3, or to embed the fluorescent material 3 into the crystal in a homogeneous or heterogeneous fashion. A photonic crystal can restrict the number of excitable cavity modes, enforce the population in allowed modes, and define the polarization of the allowed modes. The kind of distribution of the fluorescent material 3 throughout the photonic crystal can further help to excite only the wanted modes, while unwanted modes are suppressed due to improper optical pumping.

An example of photonic crystals comprising two or three-dimensional non-metallic periodic structures that do not allow the propagation of light within a certain frequency range, the so-called "bandgap" of the photonic crystal, was shown by E. Yablonovitch (Scientific American, Dec. issue, pp. 47-55, 2001). The light is hindered from propagation by distributed Bragg diffraction at the periodic non-metallic structure, which causes destructive interference of the differently scattered photons. If the periodicity of such a photonic crystal is distorted by a point defect, e.g. one missing scattering centre in the overall periodic structure, spatially confined allowed optical modes within the bandgap may occur, similar to those localized electronic energy levels occurring within the bandgap of doped semiconductors.

In the present embodiment, the optical cavity and the non-metallic core 2 are shown in spherical shape. Although such spherical shape is a very useful one, the cavity and the non-metallic core 2 may in principle have any shape, such as oblate spherical shape, or rectangular shape. According to this broad admissibility of the shape of the cavity and the core 2, the shape of the metallic shell 4 and the particle 1 may also vary.

Fluorescent material: As fluorescent material 3 any type of material can be used that absorbs light at an excitation frequency $\omega_{exc}$, and re-emits light subsequently at an emission frequency $\omega_{em}$, $\omega_{em} \cdot \omega_{exc}$. Thereby, at least one part of the emission wavelength range(s) should be located within the cavity mode spectrum of the cavity for whose excitation the fluorescent material 3 shall be used. In practice, fluorescent dyes, semiconductor quantum dots, carbon nanotubes, Raman emitters, and the like can be utilized. A Raman emitter is a material that uses the absorbed photon energy partially for excitation of internal vibrational modes and re-emits light with a frequency lower than that of the exciting light. By proper choice of the excitation wavelength many non-metallic materials may show Raman emission, so that also the core materials as described above can be used for Raman emission without addition of a particular fluorescent material 3. Examples of the fluorescent dyes which can be used in the present embodiment are shown together with their respective peak emission wavelength (unit: nm): PTP (343), DMQ (360), butyl-PBD (363), RDC 360 (360), RDC 360-NEU (355), RDC 370 (370), RDC 376 (376), RDC 388 (388), RDC 389 (389), RDC 390 (390), QUI (390), BBD (378), PBBO (390), Stilbene 3 (428), Coumarin 2 (451), Coumarin 102 (480), RDC 480 (480/470), Coumarin 307 (500), Coumarin 334 (528), Coumarin 153 (544), RDC 550 (550), Rhodamine 6G (580), Rhodamine B (503/610), Rhodamine 101 (620), DCM (655/640), RDC 650 (665), Pyridin 1 (712/695), Pyridin 2 (740/720), Rhodamine 800 (810/798), and Styryl 9 (850/830).

Semiconductor quantum dots that can be used as fluorescent materials 3 for doping the microcavities are described by Woggon and coworkers (M. V. Artemyev & U. Woggon, Applied Physics Letters Vol. 76, pp. 1353-1355, 2000; M. V. Artemyev et al., Nano Letters Vol. 1, pp. 309-314, 2001). Thereby, the quantum dots can be applied to the present embodiment in a similar manner as described by Kuwata-Gonokami and coworkers, who have shown that the fluorescence emission of dye molecules can be utilized for population of microcavity modes. The major advantage of quantum dots over dye molecules is their higher stability against degradation, such as bleaching.

The excitation wavelength $\lambda_{exc}$ of the fluorescent material 3 does not have necessarily to be smaller than its emission wavelength $\lambda_{em}$, i.e. $\lambda_{exc} < \lambda_{em}$, since one also can image multiphoton processes, where two or more photons of a given energy have to be absorbed by the material before a photon of twice or higher energy will be emitted.

In general, the fluorescent material 3 can be incorporated into the cavity material or be adsorbed on its surface. In the latter case, the metallic coating must enclose both, cavity material AND fluorescent material 3 to assure proper function. In case of incorporating of the fluorescent material 3 into the cavity material, the fluorescent material 3 can be distributed homogeneously or heterogeneously. The distribution can be used to select the type of cavity modes that are excited. For example, if the fluorescent material 3 is concentrated in vicinity of the core surface, whispering gallery modes are more likely to be excited than Fabry Perot modes. If the material is concentrated in the centre of the cores 2, Fabry Perot modes are easier to excite. Other examples of a heterogeneous distribution are those, in which the fluorescent material 3 is distributed in an ordered fashion, i.e. with regular spacing between volumes of high fluorescent material 3 concentration. In such a case, diffraction effects can occur, which help to excite the cavity in distinct directions, polarizations, and modes.

Metallic shell: The metallic shell 4 may consist of any metal that shows high transmission at the excitation frequency $\omega_{exc}$ of the chosen fluorescent material 3 and high reflectance at least in a part of its emission frequency range $\omega_{em}$. This can be achieved, for example, by utilization of the plasma frequency of the metal, above which any type of metal becomes transparent for electromagnetic radiation. Typical metals are transition metals, such as silver, aluminum, gold, titanium, cobalt and the like. The shell can be continuous, as fabricated for example via evaporation or sputtering, or contiguous as often achieved by means of colloidal metal particle deposition and subsequent electroless plating (cf. Braun & Natan, Langmuir Vol. 14, pp. 726-728, 1998, Ji et al., Advanced Materials Vol. 13, pp. 1253-1256, 2001, Kaltenpoth et al., Advanced Materials Vol. 15, pp. 1113-1118, 2003). Also the thickness of the shell 4 can vary from few nanometers to several hundreds of nanometers. The only stringent requirement is that the reflectivity of the metallic shell 4 is sufficiently high in the wanted spectral range to allow for Q-factors with values of Q >1. For spherical cavities, the Q-factor can be calculated from the reflectance of the metallic shell 4 (or vice versa) by the formula $$Q = \frac{2\pi_{cav}D}{\lambda_m} \frac{\sqrt{R_{sh}}}{1 - R_{sh}}, \tag{19}$$

where $R_{sh}$ is the reflectance of the metallic shell 4, D is the diameter of the cavity, and $\lambda_m$ the wavelength of cavity mode m. A demonstration of the Q-factors achievable with silver shells of 50 nm thickness, when dye-doped polystyrene beads are used as the core material, is given in Example 12.

Further, small holes which may be contained in the metal shell 4 are hereby examined. The metal coating is typically in the range of some tens to few hundreds of nanometers in thickness. In practice, such thin metal films often contain small defects, so-called pinholes, which actually violate the condition of encapsulation of the non-metallic particle 2 by a closed metal shell 4 according to the present embodiment. To treat this problem properly from a theoretical as well as practical viewpoint, we proceed as follows:

According to the so-called "Bethe-limit" (H. A. Bethe, Physical Review Vol. 66, pp. 163-182, 1944), the light transmission through a small aperture formed in an ideally conducting plane scales as $(r/\lambda)^4$, where r is the radius of the aperture and $\lambda$ the wavelength of the transmitted light. Obviously, the transmission decays drastically once r<$\lambda$. Hence, sub-wavelength defects in the metallic shell 4 of the order r<$\lambda$ hardly exhibit any transmission and thus do not violate the confining character of the metal shell 4 of the present embodiment. Therefore, a metal shell containing only sub-wavelength defects can still be considered as a closed metal shell 4 in the sense of the present embodiment. Such small defects may occur due to the polycrystalline character of the metal, i.e. by formation of the metal film via thermal evaporation or sputtering. Also methods involving colloidal chemistry (cf. Braun & Natan, Langmuir Vol. 14, pp. 726-728, 1998, Ji et al., Advanced Materials Vol. 13, pp. 1253-1256, 2001, Kaltenpoth et al., Advanced Materials Vol. 15, pp. 1113-1118, 2003) tend to form a contiguous film rather than an entirely closed film.

In all these cases however, the typical defect size is smaller than few hundreds of nanometers and thus the condition $r<\lambda$ is fulfilled for any wavelength $\lambda$ of the visible regime.

To give a practical limit for the maximum tolerable size of a pinhole, we consider the area of the pinhole instead of its radius to include also non-spherical pinholes. The upper limit of the condition $r<\lambda$ is $r=\lambda$, which results in a maximum tolerable pinhole area of $\pi\lambda^2$. To be in the safe region of this estimate, we set the upper limit of the maximum tolerable pinhole area somewhat arbitrarily to $$A_{ph}=\pi\lambda^2/4$$

The same result can be derived from the Abbé diffraction limit, if we assume that the minimum resolvable structure length d corresponds to the diameter of the aperture. According to Abbé, the minimum resolvable structure length d of a diffraction-limited optical system can be expressed as $$d=\lambda/N.A.,$$

where $\lambda$ is the wavelength of the light used for imaging and N.A. is the numerical aperture of the diffraction-limited system. In the case of a pinhole, N.A.=1. Thus, $d=\lambda$ and we obtain for the maximum tolerable area of the pinhole $A_{ph}=\pi(\lambda/2)^2$, which is identical to what we found above.

Excitation light source: For excitation of the cavity, a light source has to be chosen such that its emission falls into the excitation frequency range $\omega_{exc}$ of the fluorescent material 3. The emission power should be such that it can overcompensate the losses (radiation losses, damping, absorption, scattering) of excitation and emission inside of the cavity. Therefore, in practice, high power sources such as lasers or high power light emitting diodes will be preferably applied. In particular, ultrashort pulses, which excite the cavity modes only for very short time, but at high power densities, can be used. In this case, the above described quantum effects are generated only for short time and can be detected preferably by means of time-resolved read-out techniques (such as gated CCD cameras, photomultipliers connected to fast signal processing electronics, and the like).

Embodiments

Figure 4:
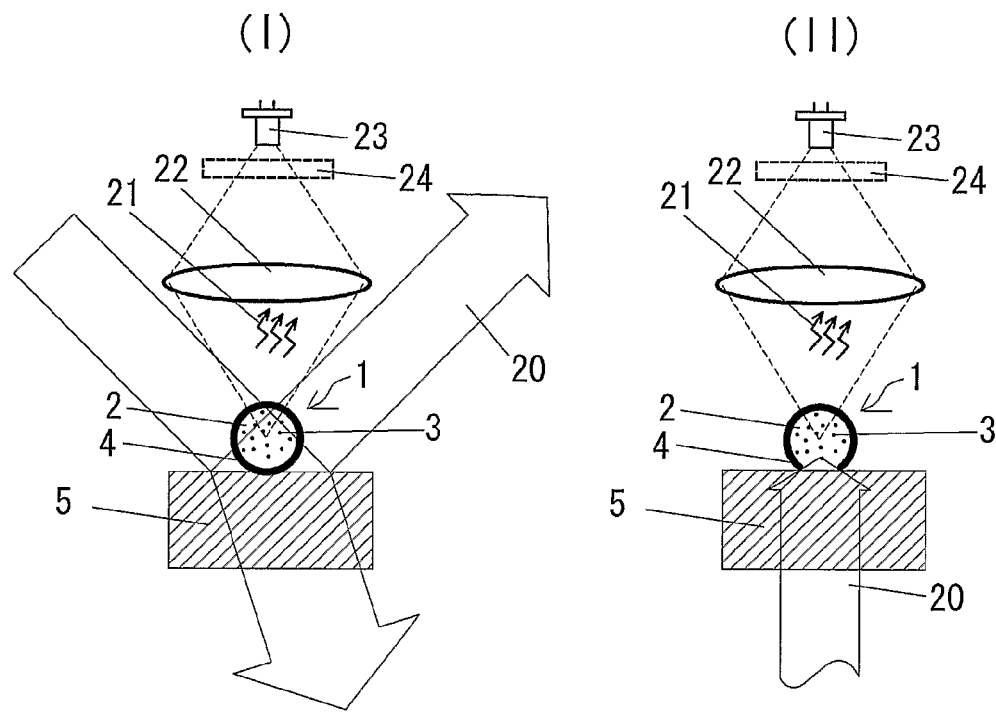
FIG. 4: Schemes for excitation and detection of optical cavity modes in a surface-adsorbed fluorescent non-metallic particle encapsulated into a metallic coating. In the case of scheme (I), the particle, consisting of a non-metallic core material containing a fluorescent material and encapsulated into a metallic coating is entirely coated with the metal and adsorbed with the metallic coating in contact with the surface. A light beam 20 used for excitation of the fluorescent material inside of the metallic coating is directed onto the surface, where it is reflected and/or transmitted, depending on the optical properties of the substrate. Due to leakage of the cavity, i.e. its finite quality factor, some light of the excited cavity modes is emergent from the particle into its outer environment, where it is collected by suitable optics, e.g. a convex lens, and guided to a photodetector. Optionally, a device containing a dispersive element, such as a filter or a grating, can be inserted into the detection path to allow spectrally resolved detection of the light emergent from the particle. In the case of scheme (II) only the free surface of the particle is coated with the metal, while that surface area in contact with the surface remains uncoated, thereby forming an optical contact between the core of the particle and the substrate. If the optical properties of the substrate are chosen properly, the excitation of the fluorescent material inside of the particle can be performed through this contact.

Excitation of Optical Cavity Modes in a Surface-Adsorbed Fluorescent Non-Metallic Particle Encapsulated into a Metallic Coating Optical cavity modes can be excited and detected in a simple manner according to the schemes shown in FIG. 4.

In the case of scheme (I), the particle 1, consisting of a non-metallic core 2 material containing a fluorescent material 3 and encapsulated into a metallic coating 4 is entirely coated with the metal 4 and adsorbed with the metallic coating 4 in contact with the surface. A light beam 20 used for excitation of the fluorescent material 3 inside of the metallic coating 4 is directed onto the surface, where it is reflected and/or transmitted, depending on the optical properties of the substrate 5. Due to leakage of the cavity, i.e. its finite quality factor, some light 21 of the excited cavity modes is emergent from the particle 1 into its outer environment, where it is collected by suitable optics, e.g. a convex lens 22, and guided to a photo detector 23. In the case of a nanoscale particle 1, also e.g. a nearfield tip can be used for detection of the cavity modes. Optionally, a device containing a dispersive element, such as a filter or a grating 24, can be inserted into the detection path to allow spectrally resolved detection of the light 22 emergent from the particle 1.

In the case of scheme (II) only the free surface of the particle 1 is coated with the metal 4, while that surface area in contact with the surface remains uncoated, thereby forming an optical contact between the core 2 of the particle 1 and the substrate 5. The term "optical contact" must be understood in the sense of enhanced transmission of light traversing the interface between the core 2 of the particle 1 and the substrate 5 in either direction as compared to the case, where the metallic shell 4 is in contact with the substrate 5 as illustrated in scheme I. If in addition the optical properties of the substrate 5 are chosen properly, i.e. the material is transparent for the excitation wavelength of the fluorescent material 3, the excitation of the latter inside of the particle 1 can be performed through this contact.

Further, the particle 1 can be partially or even entirely embedded into the substrate 5. In the latter case, the substrate 5 must be transparent at the excitation and emission wavelengths of the fluorescent material 3. In the case that the particle 1 is first surface-adsorbed and subsequently embedded into an additional material after formation of the metallic coating, the particle 1 may exhibit an optical contact to the surrounding substrate 5, similar to that discussed above.

A practical device that can be used for either scheme of this embodiment is described in Example 7 und utilized for cavity mode excitation and detection in Examples 8-11.

Figure 5:
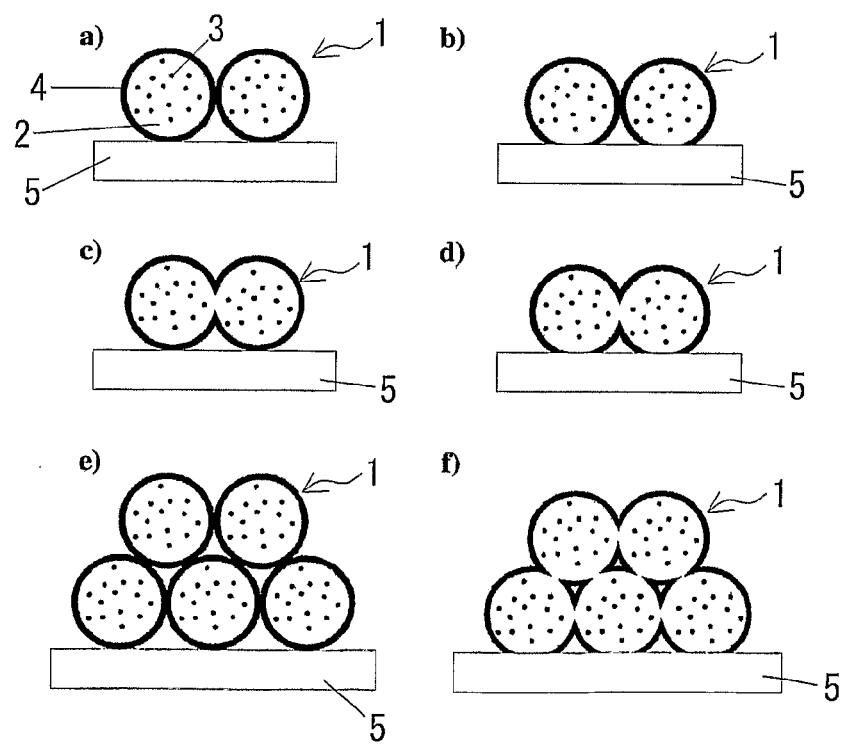
FIG. 5: Examples of systems suitable for excitation of optical cavity modes comprising more than a single fluorescent non-metallic particle encapsulated into a metallic coating. (a) two individually encapsulated, surface-adsorbed particles in close vicinity to each other; (b) two individually encapsulated particles in close vicinity to each other forming optical contacts to the substrate; (c) two surface-adsorbed particles forming an optical contact to each other, but not to the substrate; (d) two particles forming optical contacts to each other as well as to the substrate. These schemes can be easily extended to more than two particles. Also, combinations of all four schemes are feasible. To give two general examples for structures comprising more than two particles, FIGS. 5e and f show three-dimensional regular structures of surface adsorbed particles. In the case of (e), the particles are encapsulated into the metallic coating individually without optical contacts neither between the particles, nor to the substrate; in (f) the particles are arranged also in a regular fashion, this time however forming optical contacts between neighboring particles as well as to the substrate. In general, the particles or (irregular or regular) clusters of particles can be distributed over the surface in a random or an ordered fashion either in two- or in three-dimensional structures. Thereby, photonic crystals may be formed.

Excitation of Optical Cavity Modes in Clusters of Surface-Adsorbed Fluorescent Non-Metallic Particles Encapsulated into Metallic Coatings FIG. 5 exemplifies systems suitable for the excitation of optical cavity modes comprising more than a single fluorescent non-metallic particle 2 encapsulated into a metallic coating 4. In FIG. 5(*a*) two individually encapsulated, surface-adsorbed particles 1 are in close vicinity to each other. In FIG. 5(*b*) two individually encapsulated particles 1 in close vicinity to each other form optical contacts to the substrate 5. In FIG. 5(*c*) two surface-adsorbed particles 1 form an optical contact to each other, but do not provide optical contacts to the substrate 5. And in FIG. 5(*d*), two particles 1 form optical contacts to each other as well as to the substrate 5. These schemes can be easily extended to more than two particles 1. Also, combinations of all four schemes are feasible. Similar to scheme II of FIG. 4, the optical contacts between particle 1 and substrate 5 can be used for excitation of the fluorescent material 3 enclosed inside of the particles 1.

As already explained for the case of an individual particle 1, also clusters of particles 1 as described here can be partially or even entirely embedded into the substrate 5.

To give two general examples for structures comprising more than two particles 1, FIGS. 5(*e*) and (*f*) show three-dimensional regular structures of surface adsorbed particles 1. In the case of 5(*e*), the particles 1 are encapsulated into the metallic coating 4 individually without optical contacts neither between the particles 1, nor to the substrate 5; in FIG. 5(*f*) the particles 1 are arranged also in a regular fashion, this time however forming optical contacts between neighboring particles 1 as well as to the substrate 5. In general, the particles 1 or (irregular or regular) clusters of particles 1 can be distributed over the surface in a random or in an ordered fashion either in two- or in three-dimensional structures. Thereby, photonic crystals may be formed. Particularly in the case of a regular structure, there might exist certain directions of emission, the so-called "Bragg reflections" of the structure, in which the emission of individual particles 1 superimposes in an additive way, thereby enforcing the total signal.

A demonstration of cavity-mode excitation in a metal-coated trimer formed according to scheme (c) of FIG. 5 is given in Example 10.

Utilization of a Single Fluorescent Non-Metallic Particle Encapsulated into a Metallic Coating for Biosensing.

Figure 6:
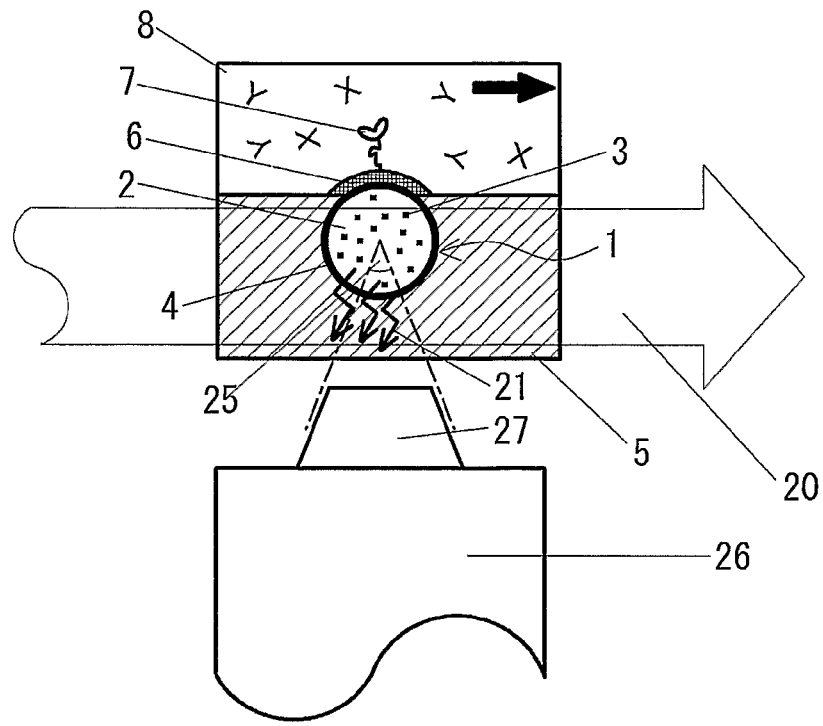
FIG. 6: Utilization of a single fluorescent non-metallic particle encapsulated into a metallic coating for a biosensing application. The particle is partially embedded in a substrate. The exposed part of the particle surface is coated with a protein-resistant matrix and one (or more) probe molecule(s) 7 for biological recognition. The substrate surface and the exposed and biofunctionalized part of the particle are mounted into a liquid cell, which provides a fluid containing potential binding partners of the probe molecule 7. The substrate is transparent for the excitation and emission wavelengths of the fluorescent material contained inside of the particle. The fluorescent material is optically pumped by a light beam 20, which propagates through the substrate, thereby also traversing the particle. The light emitted from the fluorescent material and transmitting through the metallic coating of the particle within a certain solid angle is collected by an optical fiber. The solid angle is given by the numerical aperture of the fiber and its distance from the centre of the particle. For small particles with diameters below 1 μm, the tip of the optical fiber can fabricated such, that it allows sub-wavelength resolution (Optical near field tip) to assure proper discrimination of the signal from noise.

As illustrated in FIG. 6, single particle 1 comprised of a non-metallic core 2 containing a fluorescent material 3 and enclosed by a metallic coating 4 can be utilized as biosensors in the following way:

A particle 1 is partially embedded in a substrate 5, which is transparent for the excitation and emission wavelengths of the fluorescent material 3. The exposed part of the particle surface is coated with a protein-resistant matrix 6 and one (or more) probe molecule(s) 7 for biological recognition. The substrate surface is mounted into a liquid cell 8 in such a way that the exposed and biofunctionalized part of the particle 1 comes into contact with the analyte contained in the liquid cell 8. The fluorescent material 3 is optically pumped by a light beam 20, which propagates through the substrate 5, thereby also traversing the particle 1. The light 21 emitted from the fluorescent material 3 and transmitting through the metallic coating 4 of the particle 1 due to the finite Q-factor of the cavity is collected within a certain solid angle 25 by an optical fiber 26. The solid angle 25 is given by the numerical aperture of the fiber 26 and its distance from the centre of the particle 1. For small particles 1 with diameters below 1 µm, the tip 27 of the optical fiber 26 can fabricated such that it allows sub-wavelength resolution (Optical near field tip) to provide proper discrimination of the signal from noise. Typically, such a sharpened tip 27 is controlled by means of a scanning optical near-field microscope (SNOM).

A demonstration of optical sensing by means of a single fluorescent non-metallic particle encapsulated into a metallic coating is given in Example 11.

General Setup for Biosensing by Means of Fluorescent Non-Metallic Particles Encapsulated into a Metallic Coating.

Figure 7:
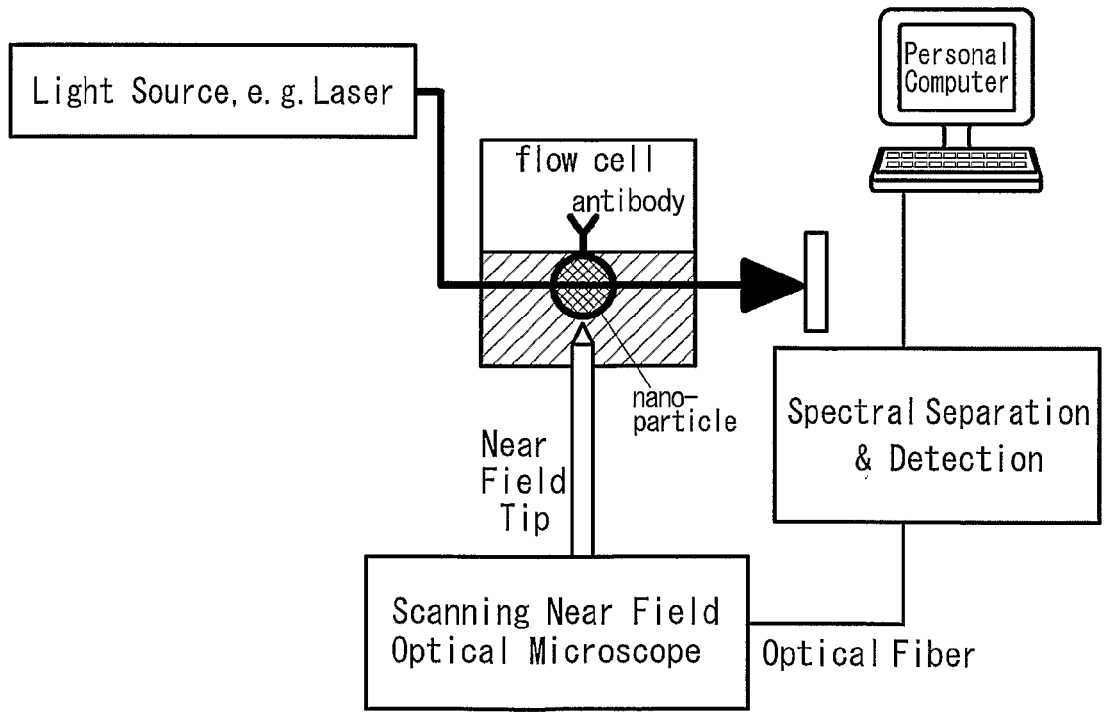
FIG. 7: General setup for biosensing by means of fluorescent non-metallic particles encapsulated into a metallic coating. The particle (or the particles) are adsorbed onto or embedded into a substrate as illustrated in FIGS. 4-6, 8, 9, and 11. The substrate is mounted into a liquid cell to allow the exposure of the exposed and biofunctionalized surface of the particle(s) to a medium containing potential specific binding partners. The fluorescent material is excited by means of a light beam 20, while the emission from the particle(s) is collected by means of a suitable optical fiber. The fiber guides the light to an optical analysis system, which records the intensity of the detected light as a function of wavelength and time.

Particles or particle systems embedded in or supported by a solid substrate 5 as described in any of the embodiments of this section, can be operated as biosensors by means of the following setup (FIG. 7): The substrate 5 is mounted into a liquid cell to allow the exposure of the exposed and biofunctionalized surface of the particle(s) 1 to a medium containing potential specific binding partners. In FIG. 7, the particle 1 is indicated as a nano-particle, though the size of the particle 1 in the embodiment is not restricted to nano size and more larger particle(s) 1 can be utilized for biosenging in the same manner shown in FIG. 7. The fluorescent material 3 is excited by means of a light beam 20 generated by a laser or another suitable light source, while the emission from the particle(s) 1 is collected by means of a suitable optical system, e.g. an optical fiber. The fiber then guides the light to an optical analysis system, which records the intensity of the detected light as a function of wavelength and time.

In a preferred embodiment, the light source used for excitation of the fluorescent material 3 is an ultrashort pulse laser, while the detection unit is able to discriminate ultrashort signals from noise. The latter can be implemented by means of a gated CCD camera or a photomultiplier connected to a fast processing electronics, such as a boxcar integrator. Ultrashort pulse lasers with sufficiently short pulses in the nano-, pico-, and femtosecond regime are commercially available.

A practical demonstration of this general set-up is given in Example 7 and utilized for cavity mode excitation and detection in Examples 8-11, and further for optical sensing in Example 11.

Utilization of Coupled Fluorescent Non-Metallic Particles Encapsulated into a Metallic Coating for Biosensing.

Figure 8:
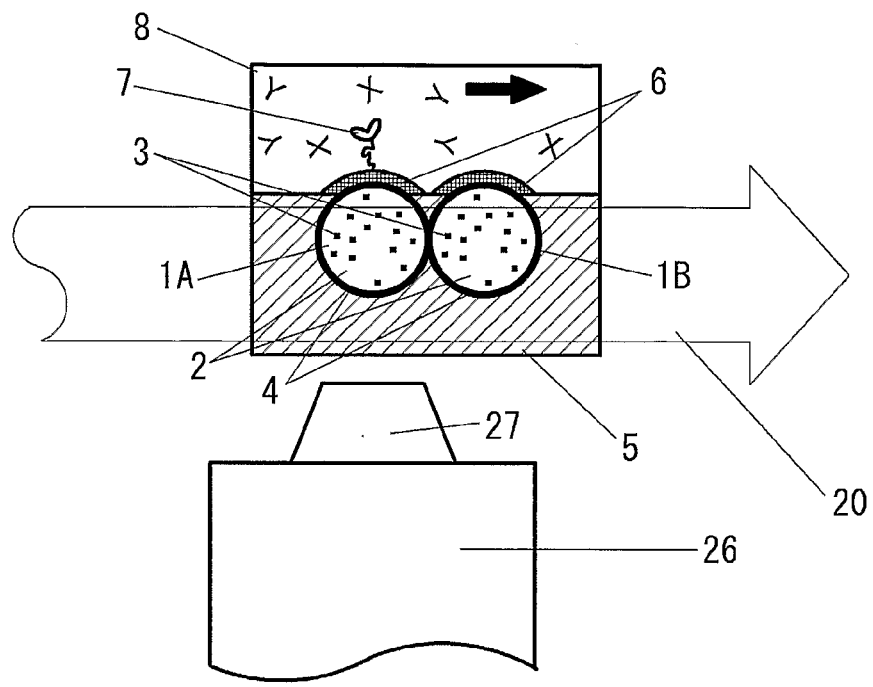
FIG. 8: Two fluorescent non-metallic particles encapsulated into a metallic coating in close contact to each other and their utilization to biosensing. Only one of the particles bears one (or more) specifically binding probe molecule(s) 7 for bio-recognition. The second particle is inert against specific binding and therefore is a measure for changes in the conditions besides specific binding events. The coupled system therefore implies an internal reference that corrects for environmental changes during the operation of the sensor. (Labels have the same meaning as in FIG. 6).

Two fluorescent non-metallic particles 2 encapsulated into a metallic coating 4 can be utilized for biosensing in the following way (FIG. 8): One of the particles 1A bears one (or more) specifically binding probe molecule(s) 7 for bio-recognition embedded into an inert matrix 6. The second particle 1B is inert against specific binding and therefore is a measure for changes in the conditions besides specific binding events. The coupled system therefore implies an internal reference that corrects for environmental changes during the operation of the sensor.

The fiber tip 27 used for detection of the signal can collect light from only one of the particles 1A, 1B or from both. The particles 1A, 1B can be fabricated either in such a way, that their cavity modes overlap spectrally or in such a way that an overlap is avoided. In the former case, mode splitting might become observable, in the latter case the reference might be operated at a wavelength better suited to trace environmental changes. Accordingly, both particles 1 may contain the same or a different fluorescent material 3 and may be pumped by the same or a different light source. Further, the particles 1 may be enclosed into a metallic coating 4 individually prior to formation of the dimer (cf. FIG. 5) or coated as an entire non-metallic system with an overall metallic coating 4. In the latter case, a non-metallic contact point has formed between the two particles 1 as illustrated in scheme (c) of FIG. 5.

A demonstration of cavity-mode excitation in a metal-coated trimer formed according to scheme (c) of FIG. 5 is given in Example 10.

System of Coupled Fluorescent Non-Metallic Particles Encapsulated into a Metallic Coating.

Figure 9:
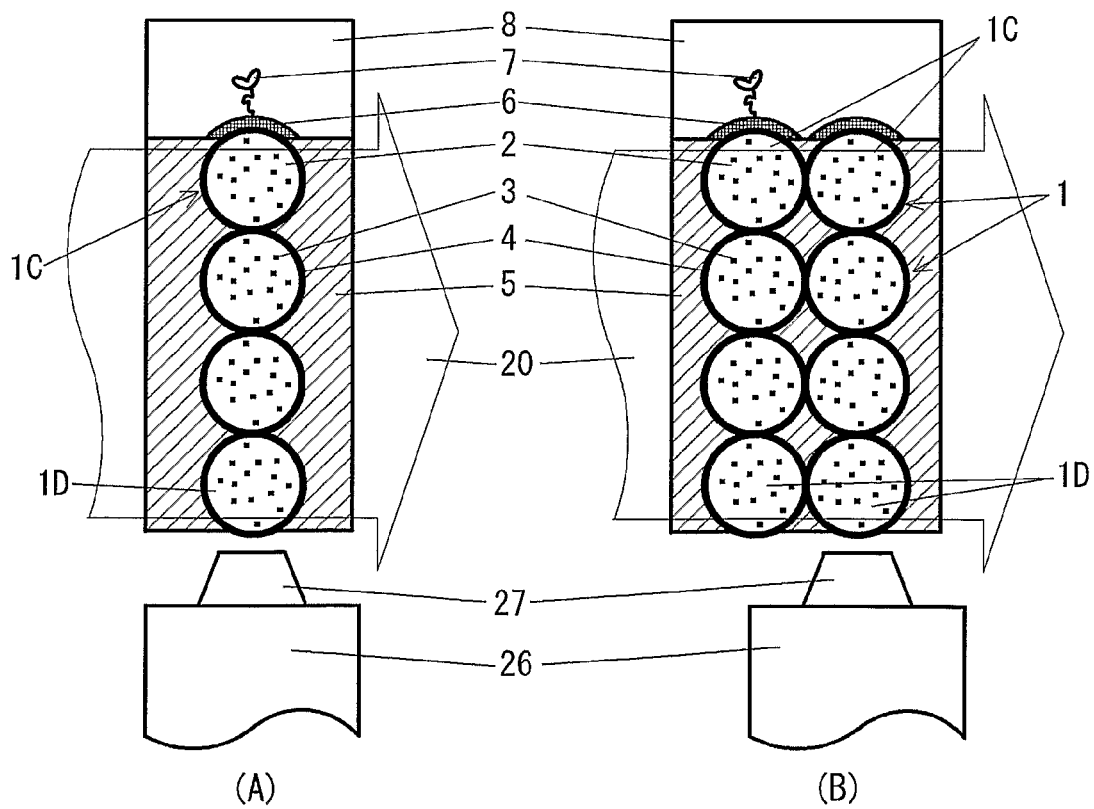
FIG. 9: System of coupled fluorescent non-metallic particles encapsulated into a metallic coating. The particles are embedded in a substrate and remain in close contact to each other. The topmost particle is partially exposed to the environment to allow biofunctionalization. Also, the particle closest to the detection fiber can be partially exposed to improve light coupling into the fiber tip. (A) system without reference line; (B) system with reference line. (Labels have the same meaning as in FIG. 6).

As illustrated in FIG. 9, the idea of particle coupling can be further expanded. The particles 1 are embedded in a substrate 5 and remain in close contact to each other such that photons can tunnel from one cavity to a neighbouring one. The topmost particle 1C is partially exposed to the environment to allow biofunctionalization. Also, the particle 1D closest to the detection fiber 26 can be partially exposed to improve light coupling into the fiber tip 27. As shown in FIG. 9, such particle systems can form stacks in one (A) or two (B) dimensions to allow biosensing without and with reference, respectively. The advantage of such systems is (i) higher signal output due to larger cross-section for optical pumping, (ii) smaller loss due to smaller surface-to-volume ratio, (iii) improved detection due to proximity between fiber tip 27 and bottom particle 1D. In fact, the lowest particle 1D can be directly optically linked to the fiber tip 27, e.g. by an index matching fluid.

In the same way as in the above embodiment, the particles 1 can be metalized prior or after formation of the particle cluster. Also, the particles 1 may contain the same or different types of fluorescent material 3. Any selection of particles 1 or the entire cluster can be used for detection by means of the fiber tip 27.

Free Floating Particles and Particle Systems.

Figure 10:
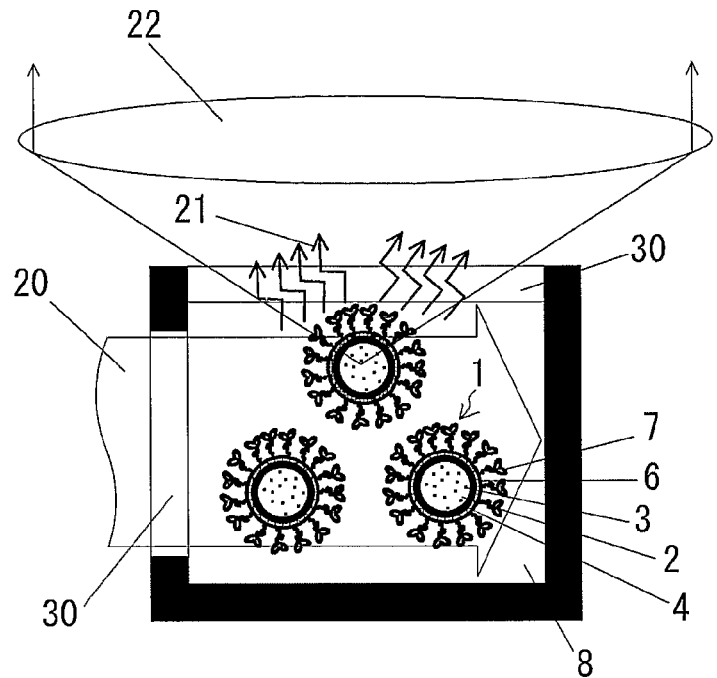
FIG. 10: Fluorescent non-metallic particles encapsulated into a metallic coating freely floating in solution. The particles float in a liquid cell (a) that contains potential specific binding partners of the probe molecule (b) bound to the particle surface. The liquid cell allows optical access to the particles 1 via an entrance window transparent for the pump light used for excitation of the fluorescent material inside of the particles and an detection window (o), which is transparent at the emission wavelengths of the fluorescent material. The emitted light (q) is collected by a convex lens (p) and guided to an optical analysis and detection system. (All other labels have the same meaning as in FIG. 6).

In another embodiment, the particles 1 are not fixed to or embedded into a solid substrate 5, but are used freely floating in the analyte (FIG. 10). Accordingly, the entire particle surface can be bio-functionalized, thereby increasing the sensitivity of an individual particle 1. Particles 1 can either be isolated or form clusters. Also, they can bear an inert matrix 6, into which the specifically binding probe molecules 7 are embedded. For detection of specific binding events, the liquid cell, which contains the analyte, must provide optical access at the excitation and emission wavelengths of the fluorescent materials 3. The same or different optical windows 30 can be used for excitation and detection of the emitted light 21, respectively. Also, more than a single light source can be used for their excitation. Since the particles 1 are freely floating, a time-resolved excitation and detection using ultrashort light pulses is a preferred embodiment in this case. Further, the particles 1 may contain more than one fluorescent material 3 to widen the operating spectral range of the cavities. Accordingly, a larger number of cavity modes can be used for analysis and determination of the amount of adsorbed biomolecules on the outer surface of the particles 1. This is important, because no reference measurement can be performed on the particles 1 prior to biomolecular adsorption, thereby demanding for acquisition of improved information on the system during a single measurement.

Alternative Detection in the Case of Many Emitters Resting on or Embedded into a Substrate.

Figure 11:
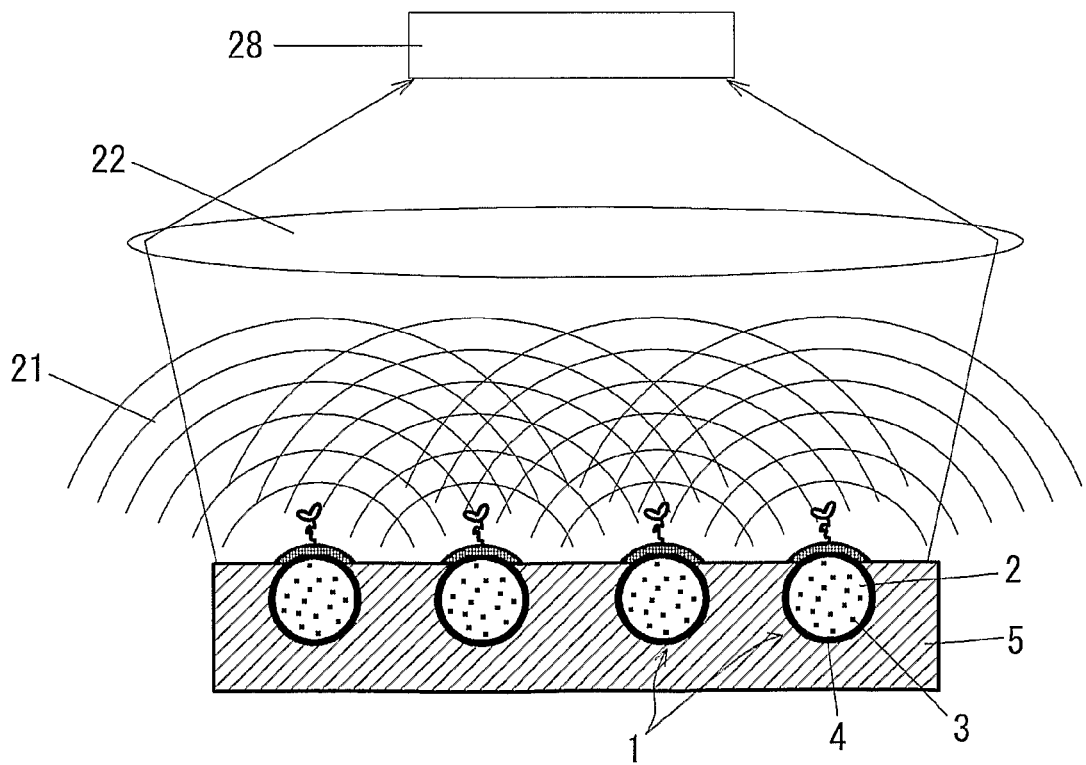
FIG. 11: Alternative detection in the case of many emitters (sensors) embedded into a substrate. The light (c) emitted by the individual emitters is collected by means of a convex lens (b) and imaged onto the chip (a) of a CCD camera in such a way, that the interference pattern of the particles can be monitored. Any change in the state of an individual emitter causes an immediate change in the interference pattern that can be further analyzed.

In the case that many fluorescent non-metallic particles 2 encapsulated into a metallic coating 4 are either resting on or (partially) embedded into a surface 5 and used for biosensing, detection of the individual signals with an optical fiber or bunches of optical fibers might become too tedious. In such a case, an alternative method might be applicable (FIG. 11): The light 21 emitted by the individual emitters is collected by means of a convex lens 22 and imaged onto the chip 28 of a CCD camera in such a way, that the interference pattern of the particles 1 is imaged and recorded by the CCD. Any change in the state of an individual emitter causes an immediate change in the interference pattern. The pattern can be recorded prior to exposure of the analyte to obtain a reference. If the time resolution of the detection system is high enough, in-situ monitoring of fluctuations in binding and related effects become observable on the micro- and nanoscale. The information on changes can be extracted from the interference patterns by analytical methods, such as Fourier transformation and related techniques.

Other Applications.

The fluorescent non-metallic particles encapsulated into a metallic coating 4 in accordance with the present embodiment form a novel type of microscopic light source, because the light populating the cavity modes can escape from the cavities due to their moderate Q-factors, which range typically between 10 and some 100. Since mostly Fabry-Perot modes are excited, the microcavities form a novel type of microscopic spherical wave source. In the case that the cavities are pumped with an ultrashort pulse laser, at least some of the cavity modes may fulfill the lasing condition. For these modes, then, a spherical wave laser has formed. Such small spherical wave light sources are useful for a number of applications due to their coherence, radiation power and overall size. We give some examples in the following:

In-line holography: In-line holography utilizes coherent spherical waves emerging from sub-wavelength apertures for microscopy at a resolution below the Abbé diffraction limit (W. Xu et al., Proc. Natl. Acad. Sci. USA Vol. 98, pp. 11301-11305, 2001).

The spherical wave is partially scattered from an object. Then, the interference pattern resulting from the interference between scattered and non-scattered wavelets of the spherical wave is recorded by means of a CCD camera. This hologram is back-transformed into a real space image. Besides its high spatial resolution, the main advantage of the method is that the hologram contains the entire three-dimensional information of the object. Particular applications are in biology and biochemistry, since bio-matter is typically only weakly absorbing in the UV-visible region of the electromagnetic spectrum.

A major bottleneck of the method is the fabrication and control of the pinhole aperture required to form the spherical wave. Pinholes of some hundreds of nanometer in diameter are difficult to fabricate and to handle. Here, our approach provides a unique solution to this problem. The spherical wave emerges from the particle 1. The particle 1 can be bio-functionalized and e.g. also magnetized. Then, it can be brought to any place within the biological sample under investigation and undergo specific interactions. While these interactions proceed, the spherical waves emerging from the particle 1 can be used for in-situ imaging of the biological events.

Display technology: Sub-wavelength sources for spherical waves are similar to the Huygens principle of elementary wavelets. According to this principle, all propagating light waves can be thought of emerging from densely packed nanoscopic sources of spherical waves, which interfere destructively in most directions, except for the directions of light propagation. By means of the particles 1 described here, this principle can be practically implemented into surfaces, similar to the approach illustrated in FIG. 11. Depending on the way the particles 1 are excited, the interference pattern can be controlled, thereby allowing the development of new types of optical displays.

EXAMPLES

Example 1

Sensitivity Estimate for Spherical Cavities Based on Quantum Interference Effects This example gives an estimate on the expected sensitivity of a single cavity with respect to biomolecular adsorption, if the cavity volume is chosen as small as possible for the wavelength, at which the cavity is operated (according to eq. 5a). We chose realistic materials, which can be purchased, e.g. from Polysciences, Inc. 400 Valley Road, Warrington, Pa. 18976.

Given:

1. Polystyrene beads with a refractive index of $n_{cav}=1.60$ and doped with dye molecules, which emit light at an emission wavelength $\lambda_{em}=420$ nm 2. Antibody with a volume of $(10 \text{ nm})^3$ Further assumptions: For calculating a sensitivity estimate, we further assume that 1. The refractive index of the antibody is larger than that of the surrounding of the cavity, in fact, we assume that it is the same as that of the cavity material. Then, the adsorption of a biomolecule on the outer surface of the cavity causes an increase of its effective diameter just according to the deposited volume. Effects of the metallic coating 4 are neglected, since it can be made sufficiently thin.

2. A single antibody is thought to be homogeneously distributed over the entire surface area of the cavity. This is a save assumption, since in this case the change in diameter is minimal and no symmetry changes of the cavity shape do occur. The latter are known to cause additional effects on the cavity modes, such as mode splitting. Therefore, the shifts of the cavity modes due to adsorption of a bulky antibody can be expected to be even larger.

Estimate:

Under these assumptions, the minimum particle radius as resulting from eq. 5a is $R_{min}=102.5$ nm. Then, the effective change in R, δR, for a single antibody adsorbed on the particle surface (assuming that the antibody is homogeneously distributed over the entire surface area) amounts to δR=7.5 pm. This results in $$\frac{\Delta\omega}{\omega} = \frac{\Delta R}{R} = \frac{0.0075}{102.5} = 7.3 \times 10^{-5}.$$

At 420 nm, the operating wavelength of the cavity, this corresponds to a frequency shift of 1.75 cm$^{-1}$ or Δλ=0.031 nm, which is easily detectable with state-of-the-art spectrometers. Therefore, single antibody detection by means of a single nano-cavity seems to be possible under the chosen conditions. If a larger number of antibodies can be used for generation of the input signal of the sensor, the cavity may become much larger. Assuming that a monolayer of antibodies forms on the entire cavity surface yields δR=10 nm. Therefore, even for a cavity with R=10 μm, the resulting wavelength shift amounts to 0.42 nm (corresponding to 23.8 cm$^{-1}$) at 420 nm, and therefore is easily detectable. For formation of a monolayer, about 12.6 million antibodies would be required (given a volume of (10 nm)$^3$ per antibody) in this case. Therefore, the utilization of smaller particles 1 with smaller surface area is advantageous.

In Example 11, a silver-coated dye-doped polystyrene bead with a nominal diameter of 10 μm is applied to optical sensing by monitoring its cavity modes. The shift in the resonance position of the modes due to formation of a monolayer of hexadecanethiol (HDT) on the silver surface amounts to 3 nm. The refractive index of this monolayer is about $n_{HDT}$=1.45 and thus lower than what we assumed for the antibody in above calculation. Further, its thickness amounts to about 2 nm. Accordingly, the observed shift is larger than expected from the above calculation, which accounts only for the increase in size due to molecular adsorption on the cavity surface. In Example 11, however, the thickness of the silver shell amounts to 50 nm and thus is not "sufficiently thin". Accordingly, additional effects, such as contributions from surface plasmon excitations, add to the basic dependency discussed here, and we can consider the latter as a save lower limit for the expected effects.

Example 2

Estimated Radiative Power of a Single Nanocavity Due to Purcell Enhancement

Example 1 shows that the sensitivity of a nanocavity with a diameter of 205 nm and operated at a wavelength of 420 nm (emission wavelength of the dye incorporated inside of the cavity) should be high enough for single antibody detection. However, high sensitivity alone does not help for construction of a nano-biosensor if the signal, the sensor radiates, is too weak. Therefore, in this example we give an estimate on the expected radiative power of the system discussed in example 1.

Further Assumptions:
1. Dye molecules inside of the cavity have a density of 0.1/nm$^3$ and a dipole moment typical for organic dyes, d=2×10$^{-29}$ C×m
2. Further, we assume a Q-factor of Q=100, which in the case of a metal-coated cavity would correspond to a reflectivity of the metallic shell coating 4 of $R_{sh}$=97% according to eq. 19 and with all other parameters as given above.

Estimate:
Under these assumptions, the spontaneous emission rate $\gamma_{SE}$ amounts to $\gamma_{SE}$=7.42×10$^9$ Hz at 420 nm per dye molecule according to eq. 6. Given that 4500 dye molecules are present in the cavity (corresponding to 0.1 dye molecules per nm$^3$), this corresponds to a total radiative power of 16 μW, which is easily detectable with state-of-the-art optical detection systems (for example, a scanning near field optical microscope could be used for collection of the emitted radiation. A photomultiplier tube could be used for its subsequent detection). The enhancement due to the presence of the cavity, i.e., the Purcell factor $\eta_{cav}$, amounts to $\eta_{cav}$=30. Therefore, without Purcell enhancement, the signal of the nano-biosensor would be very difficult to detect (~500 nW total power).

Example 3

Sensitivity of Nanocavities Due to Cavity Mode Splitting

At small cavity sizes close to the minimum volume according to eq. 5a, other quantum effects, such as mode splitting of the cavity modes can occur. Since at the very size limit, only a single cavity mode can be excited, this splitting is very interesting, because it allows for the determination of a relative separation between the two split modes rather than the measurement of an absolute position of a single mode. The former might turn out to be more reliable and less affected by changes in the environment of the nanocavity, such as temperature changes, etc. Therefore, the mode splitting might become relevant for the improvement of stability and reliability of nano-biosensors. According to eqs. 8-10 and assuming the same values for all parameters as in the examples above, a change in the mode splitting of about 3 cm$^{-1}$ can be expected for the adsorption of 130 antibodies (volume (10 nm)$^3$ each) on the surface of a particle 1 with R=102.5 nm. Thus, in principle, utilization of changes in the mode splitting is less sensitive than observing the absolute peak position. In practice however, this additional information might help to interpret the shifts detected in the absolute position of the cavity mode, and thus improve the overall performance of the nano-biosensor.

Example 4

Emitter-Cavity Coupling

As outlined above, the relations between cavity and emitter parameters to achieve strong coupling is governed by the ineq. 15. Following the above example with an emission wavelength of $\lambda_{em}$=420 nm, a refractive index of the cavity core of $n_{cav}$=1.60, a core radius of R=102.5 nm, and a dipole moment of the fluorescent material 3 of d=2×10$^{-29}$ C×m, a lower limit for the Q-factor of the cavity of Q=5500 can be calculated.

Example 5

Reflectivity of Metals and Optical Properties of Silver

Figure 12:
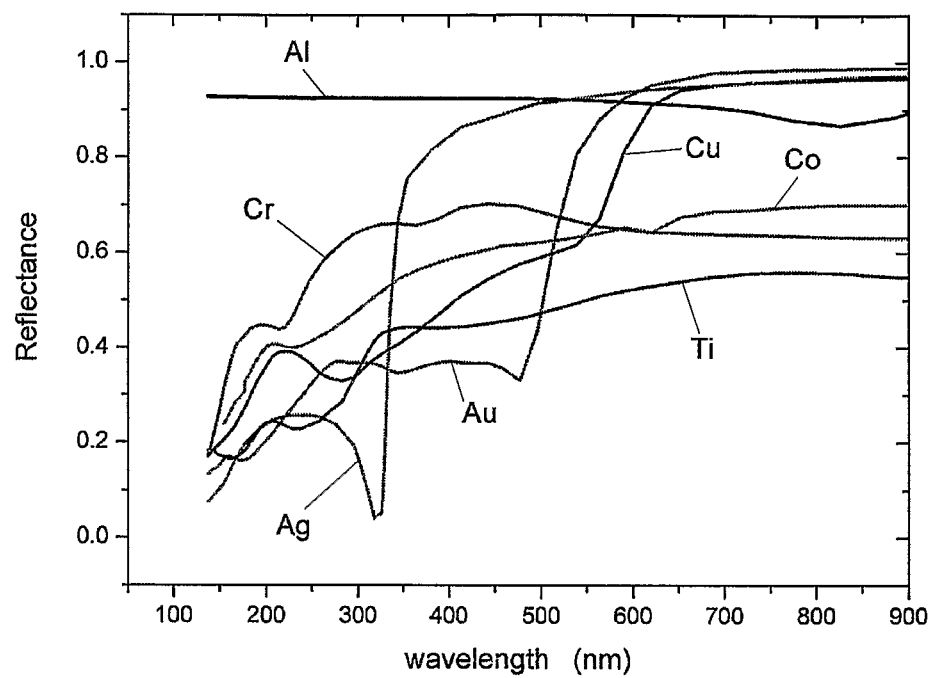
FIG. 12: Reflectance of metals at different wavelength (data taken from the Handbook of Chemistry and Physics, 70th ed., CRC press, Boca Raton, Fla.).

The metallic shell 4 may consist of any metal that shows both of low reflectance at the excitation frequency $\omega_{exc}$ of the chosen fluorescent material 3 and high reflectance at least in a part of its emission frequency range $\omega_{em}$. Typical metals satisfying this condition are transition metals, such as silver, aluminum, gold, titanium, cobalt, copper, chromium and the like. Especially, from the view points of availability and handleability, silver, gold, and copper are more suited as the metallic shell 4. Further, it is shown in FIG. 12 that silver shows the most clear difference between low reflectance at the wavelength around 320 nm and the high reflectance at the wavelength more than 400 nm. Therefore, it is more preferable to choose silver as a material for fabricating the metallic shell 4.

As one example of the switching behavior of the reflectance of metals at the plasma frequency, i.e. low reflectance at frequencies above the plasma frequency and high reflectance at frequencies below, we discuss the optical properties of silver in the following. Tabulated values of the reflectance, R, for normal incidence, the refractive index n, and the absorption coefficient k are taken from the Handbook of Chemistry and Physics, 70$^{th}$ edition, CRC Press, Boca Raton, Fla., page E-401. The complex refractive index N is then given as N=n+ik.

Figure 13:
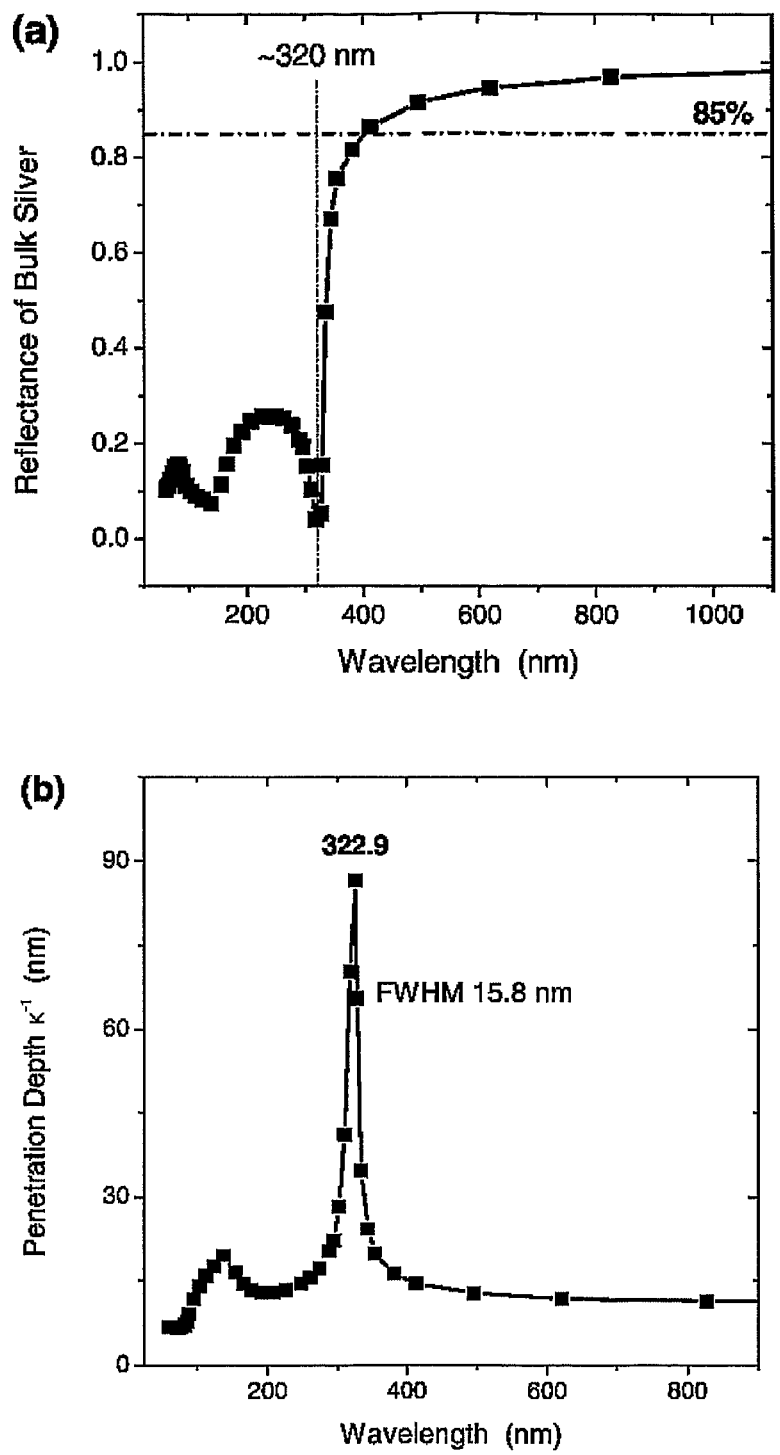
FIG. 13: (a) Tabulated values for the reflectance of bulk silver as a function of wavelength; source: Handbook of Chemistry & Physics, $70^{th}$ ed., CRC press, Boca Raton, Fla., 1989; (b) Wavelength dependence of the penetration depth of light into bulk silver as calculated from the tabulated data of refractive index and absorption coefficient given in the Handbook of Chemistry & Physics, $70^{th}$ ed., CRC press, Boca Raton, Fla., 1989.

FIG. 13(a) displays the tabulated values of the reflectance R of silver as a function of wavelength. It can be clearly seen that the reflectance R is above 85% for wavelengths above 415 nm and drops very rapidly below 400 nm to give a pronounced minimum around 320 nm, which can be attributed to the location of the plasma frequency of silver. At 318 nm the reflectance amounts to only 4%. Accordingly, light of this wavelength can penetrate into silver to high fraction. For excitation of a fluorescent material 3 through a metal coating 4 it is important, however, that the light penetrating into the metal is not entirely absorbed. Since in general, the equation $$R+A+T=1 \tag{20}$$

holds, where R is the reflectance, A the absorbance, and T the transmittance of a material, it becomes clear that a low reflectance does lead to a high transmittance only in the case of a low absorbance. The absorbance, A, depends on the travel length z of light travelling through the material $$A(z) = 1 - \frac{I(z)}{I(z=0)} = 1 - \exp(-\kappa z), \tag{21}$$

where $\kappa$ is the so-called "absorption constant" and I(z) is the intensity of the travelling light after a distance z. Equation 21 shows that after a travel length of $z=\kappa^{-1}$, the initial light intensity has dropped to a relative magnitude of exp(−1) ≈36.8%.

$\kappa$ can be calculated from the absorption coefficient k of a material according to $$\kappa = \frac{4\pi}{\lambda} k, \tag{22}$$

where $\lambda$ is the vacuum wavelength of the traveling light. The penetration depth, $\kappa^{-1}$, as calculated from the tabulated values for the absorption coefficient of silver is also displayed in FIG. 13(b). While the metal exhibits high absorbance, i.e. a small penetration depth almost in the entire spectral range shown, there is a sharp maximum around 320 nm. This means that the earlier discussed low reflectance is accompanied by a reduced absorbance and according to equation 20 an enhanced transmittance can be expected in this spectral region. However, the absorbance is not zero and therefore also in this spectral region the metal shows finite absorption, thus rendering any macroscopic silver sample opaque. FIG. 13(b) shows, however, that a thin film of silver with a thickness in the range of 50 nm should still be transparent to about 37%. In other wavelength regimes, i.e. in the visible regime, a silver film of such thickness should be already basically opaque.

The tabulated values of the optical properties of silver are measured for bulk samples. It wonders therefore, if a thin film of silver with a thickness in the range of some tens of nanometers shows the wanted properties, i.e. high transmittance around 320 nm and high reflectance in the visible regime. Then, silver could be used as the metal shell of the present embodiment.

Figure 14:
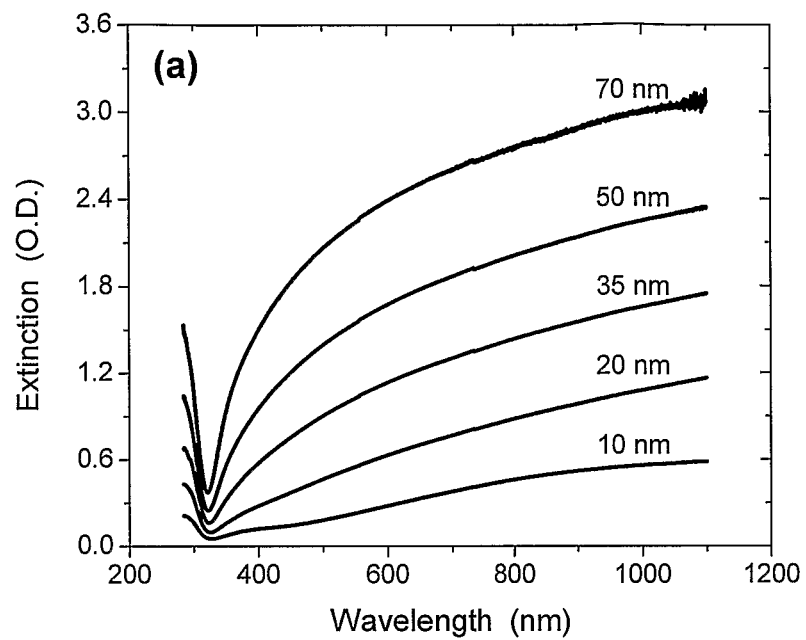
FIG. 14: Measured extinction (a) and transmittance (b) of thin films of silver evaporated by means of thermal evaporation onto plain polystyrene substrates of 1 mm thickness. A non-coated polystyrene substrate of same type was used as reference.
Figure 14:
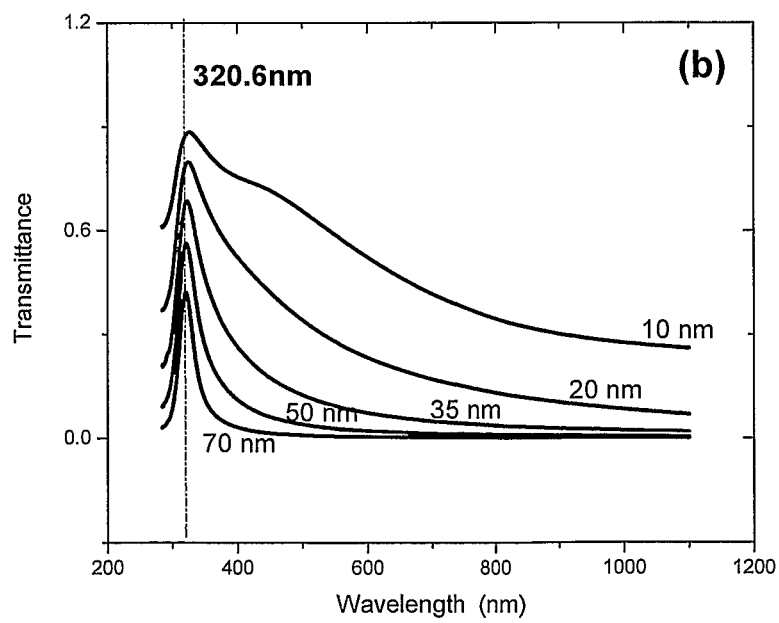

To prove the transmission and reflection properties of thin films of silver, we evaporated silver by means of thermal evaporation (Auto 306, Edwards High Vacuum Intl., Crawley, UK) onto flat polystyrene substrates 5 (lids of cell culture dishes, CAT# 430165, Corning, Inc., NY) and measured the transmission in the UV-visible range at normal incidence with a UV-vis spectrometer (DUV-630, Beckman-Coulter, UK). The resulting transmission and extinction (extinction=absorbance+reflectance) spectra are displayed in FIG. 14 for different thicknesses of the silver film. At low thickness, the silver film exhibits only weak wavelength dependence in extinction and transmittance, respectively, which however increases significantly with increasing thickness. Table 1 shows experimentally determined transmittance through thin films of silver evaporated on a polystyrene substrate for two different wavelengths as a function of film thickness. Given is further the ratio of the transmittances at the two wavelengths, thereby indicating the switching behavior of silver below and above the plasmon resonance.

The maximum of the transmittance around 320 nm shows a blue-shift from 327.0 nm at 10 nm thickness down to 320.6 nm at 70 nm silver film thickness. In Table 1, we chose 320.6 nm as wavelength with high transmittance and 496.0 nm as an example for a wavelength in the visible regime with low transmittance. As can be seen from the Table 1, the switching behavior of the thin silver films, i.e. the ratio of T(320.6 nm)/T(496.0 nm) increases significantly in the range from 35 to 70 nm film thickness. While this ratio is expected to increase further with increasing thickness, it is not advisable to use much thicker silver films due to the increasing absorptive losses and accompanied heating effects inside of the shell. On basis of the tabulated values for the complex reflective index and the reflectance of bulk silver, we estimate silver film having thicknesses preferably between 10 and 70 nm, more preferably between 50 and 70 nm, is the most suited as metal shells of the present embodiment. As a proof of this procedure, a comparison of calculated and measured total transmittance from the tabulated values with that determined experimentally through a 20 nm and 50 nm thick silver film, respectively, deposited onto a polystyrene substrate for two different wavelengths (cf. FIG. 14) is given in Table 2. As can be seen readily, the results show good agreement, thereby justifying the use of the tabulated values for the extrapolation of the suitable range of the silver thickness.

Altogether, the results show that silver exhibits a pronounced switching behavior in its transmittance around its plasma frequency and already thin films of silver in the range from 30 to 100 nm exhibit sufficient contrast in transmittance between plasma frequency and the visible regime, respectively, to allow an application as the metal shell of the present embodiment.

Preferable material for fabrication of the core 2 may vary depending on the material consisting of the metal shell 4. In particular, the core material must be resistant to the fabrication process of the metallic shell 4. For example, by use of low vacuum thermal evaporation, the core material may not degrade due to the temperature rise in the course of the evaporation. Therefore, inorganic core materials with high melting points may be better suited in such case. Further, the core material may bear particular chemical functionalities, which facilitate the formation of a metallic shell 4 around the core particle 2. These can be, for example, ionic groups or functional groups, such as carboxylic, hydroxyl, or amino groups. The metallic shell 4 can then be formed, for example, via colloidal chemistry, as described by Braun & Natan, and Kaltenpoth et al. (cf. Braun & Natan, Langmuir Vol. 14, pp. 726-728, 1998, Ji et al., Advanced Materials Vol. 13, pp. 1253-1256, 2001, Kaltenpoth et al., Advanced Materials Vol. 15, pp. 1113-1118, 2003). In the case of electroplating of the metallic shell 4, the core material may not degrade in the presence of the required electrolytes. To give a practical example, it has been reported in the literature that sulfonated polystyrene beads can be coated with contiguous gold shells by means of colloidal chemistry (Kaltenpoth et al.). However, it was found that for formation of a silver shell, e.g. by means of the Tollens reaction (Antipov et al., Langmuir Vol. 18, pp. 6687-6693, 2002), carboxylated polystyrene beads are better suited than sulfonated, because the carboxylic functions can be directly involved into the chemical reaction.

TABLE 1

| | Ag Thickness (nm) | | | | |
| --- | --- | --- | --- | --- | --- |
| | 10 | 20 | 35 | 50 | 70 |
| T (320.6 nm) (%) | 87.47 | 78.73 | 68.50 | 56.04 | 42.22 |
| T (496.0 nm) (%) | 66.22 | 34.79 | 12.80 | 4.14 | 0.90 |
| T (320.6 nm)/T (496.0) | 1.32 | 2.26 | 5.35 | 13.54 | 46.91 |

TABLE 2

| | 326 nm | | 496 nm | |
| --- | --- | --- | --- | --- |
| | Exp. | Theo. | Exp. | Theo. |
| 20 nm | 79.7% | 75.2% | 34.9% | 19.8% |
| 50 nm | 53.6% | 53.1% | 4.2% | 1.9% |

Example 6

Transmittance and Absorbance of Silver-Coated Polystyrene

Figure 15:
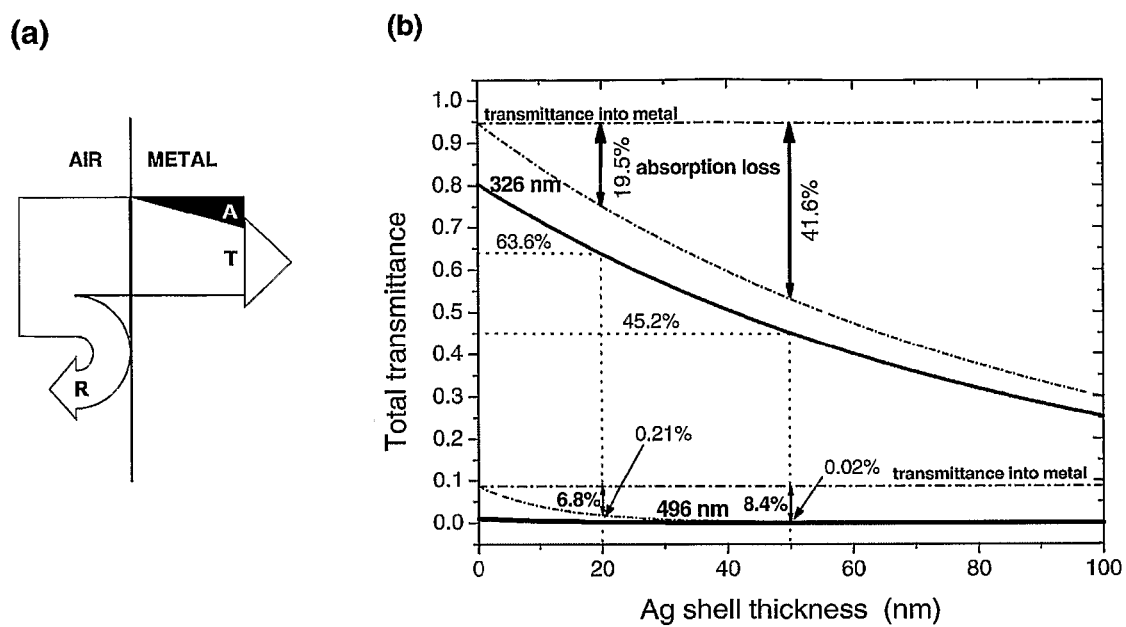
FIG. 15: (a) Scheme for the relation between reflection, absorption, and transmission at an air/metal interface; (b) Total transmittance of visible light impinging from the outside onto a silver-coated polystyrene substrate into this substrate as a function of the thickness of the silver film. The calculation is based on the tabulated data of refractive index and absorption coefficient for silver given in the Handbook of Chemistry & Physics and the known refractive index of polystyrene of 1.59.

For the excitation of a fluorescent material 3 embedded in a non-metallic core 2 material that is encapsulated by a metallic shell 4 the total transmittance of light at the excitation wavelength of the fluorescent material 3 through the metal shell into the non-metallic core 2 material is crucial. Also, the absorption losses inside of the metal shell should not be too excessive to avoid unwanted thermal effects. As an example, we calculate the total transmittance and absorbance of a polystyrene substrate 5 coated with a thin film of silver for two different wavelengths. We assume that light of a given wavelength impinges from the ambient (air or vacuum) onto the silver film, penetrates this film to a certain fraction, and then enters the polystyrene substrate 5. The fraction of intensity that enters the polystyrene is called "total transmittance" in the following. A schematic of the first interface and the loss mechanisms reducing the transmittance into the metal is displayed in FIG. 15(a). According to equation 20 the transmittance T is affected by a reflection loss R immediately at the interface and an absorption loss A in the course of propagation through the metal. Using the tabulated values for the complex refractive index of silver already used above and assuming a refractive index of the polystyrene substrate 5 of $n_{PS}=1.59$, we can calculate the total transmittance for perpendicular incidence using the Fresnel formulas for reflection and equations 20 and 21. The result is shown in FIG. 15(b) for two different wavelengths. At 326 nm the reflection loss at the interface is very low, so that about 95% of the incident light penetrate into the metal. Due to absorption inside of the metal, this intensity drops in the course of propagation through the metal and thus depends on the silver film thickness as indicated by the dash-dotted line. At the silver/polystyrene interface another reflection loss occurs, resulting in the thick line marked as "326 nm". This shows, for example, a total transmittance into the polystyrene substrate 5 of 63.6% at a silver film thickness of 20 nm and of 45.2% at a thickness of the silver film of 50 nm, respectively. The absorption losses for these two silver film thicknesses amount to 19.5% and 41.6%, respectively, as indicated by the black arrows.

The same calculation for a visible wavelength of 496 nm yields a high reflection of more than 95% at the air/metal interface and a fast decay due to internal absorption. The total transmittance amounts to 0.21% in the case of the 20 nm silver film and to 0.02% in the case of the 50 nm film. The absorption losses are 6.8% and 8.4%, respectively, which is lower than for 326 nm, since only a small portion of light penetrates into the metal at all. This calculation shows that a significant portion of UV light can still penetrate into a silver-coated polystyrene particle, even when the silver shell is already highly reflective for visible light.

Example 7

Optical Set-Up for the Study of Cavity Modes in Microscopic Particles

Figure 16:
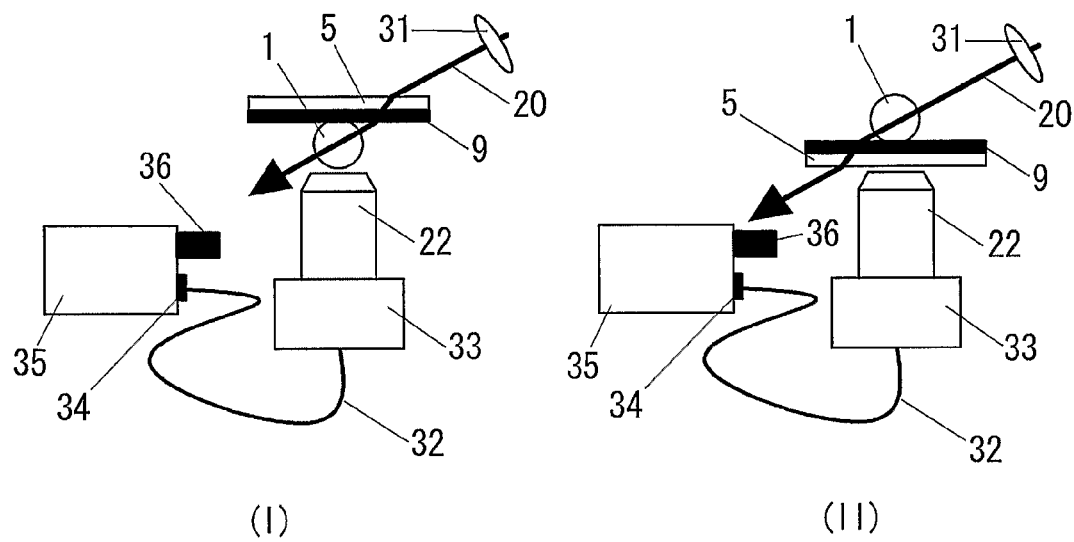
FIG. 16: Optical set-up used in the examples. (I) Sample placed upside down onto the sample stage of an inverted microscope to allow collection of the fluorescence emitted from a particle deposited on a thick substrate by means of a 100× microscope objective with a working distance of 0.2 mm; (II) Sample placed in upright position in case of a sufficiently thin substrate.

A set-up suitable for excitation and detection of cavity modes in microscopic particles 1 is displayed in FIG. 16. A sample, which typically consists of a substrate 5, an optional metal-coating 9, and a fluorescent particle 1, is either placed upside down onto the stage of an inverted microscope (Nikon Eclipse TS 100) in scheme (I) or with the particle 1 pointing upwards, i.e. away from the collection lens 22 (Nikon, 100×, N.A. 1.3 oil) of the microscope in scheme (II). The main reason for these two options is the small working distance of the collection lens 22 of about 0.2 mm. Hence, the substrate 5 bearing the particle 1 must be thinner than 0.2 mm to allow use of detection scheme (II). To assure that no interference effects, which might be misinterpreted as cavity modes of the particle 1, are caused when applying such a thin substrate 5, thicker samples may be analyzed by means of detection scheme (I).

For fluorescence excitation of the particle 1, the laser emission 20 is focused onto the sample via a convex 100 mm silica lens 31 (CAT# LA4600-UV, Thorlabs Japan, Inc., Tokyo, Japan). The beam focus is in the range of several tens of microns and therefore always larger than a single bead. Thus, a sparse decoration of the substrate 5 with beads is crucial for excitation of a single bead only.

The light emitted from the particle 1 is collected by the lens 22 and coupled into an optical fiber 32 (multimode, 200 μm core diameter) via a coupling optics 33 mounted to the camera port of the microscope. The fiber 32 guides the light to the detection system, consisting of an optical absorbance filter 34 to eliminate stray light of the laser (GG400 for UV from 310 to 325 nm, and OG550 for 532 nm excitation, Schott Glas, Mainz, Germany), a high resolution monochromator 35 (Triax 550, Horiba Jobin Yvon, Kyoto, Japan, or SP2500, Nippon Roper, K.K., Tokyo, Japan), and a CCD camera 36 (iDus DV420A-BV, Andor Technology, Belfast, Northern Ireland, or PI-MAX:512, Nippon Roper, K.K.). The CCD cameras 36 is connected to a personal computer by means of a USB connection for data acquisition and processing. In the experiments described below, the monochromators were either equipped with 300 L/mm, 600 L/mm, and 1200 L/mm gratings (Triax) or 150 L/mm, 1200 L/mm, and 1800 L/mm (SP-2500). Typical acquisition times of the CCD were 60 s in the case of shutter mode operation (iDus and PI-MAX) or a total of 800000 gates at 20 kHz repetition rate in the case of gated mode operation (PI-MAX only). If other acquisitions times were used, the intensity was linearly scaled accordingly to allow direct comparison with the spectra acquired for 60 s.

As light sources, either a continuous wave (cw) helium-cadmium (HeCd) laser with dual wavelength emission at 325 nm and 442 nm, respectively, was used (Kimmon Lasers, Tokyo, Japan) or a pulsed Nd:YAG laser (10 ps pulse duration, 20 kHz repetition rate) equipped with a second harmonic generation (532 nm) stage and a custom-made optical parametric generator (310-330 nm) was applied. The laser intensity could be adjusted by rotating a $\lambda/2$ plate put into the laser beam 20 in front of a polarizer set to p-polarization. Irrespective of the laser used, the beam 20 was guided through an iris aperture set to about 2 mm diameter, before the beam 20 was guided through lens 31 onto the sample, thereby setting the beam diameter to a well-defined value.

For measurement of the laser intensity, a Coherent Field-Mate laser power meter equipped with a PS10Q power head was used (Coherent Japan, Inc., Tokyo, Japan).

Example 8

Figure 17:
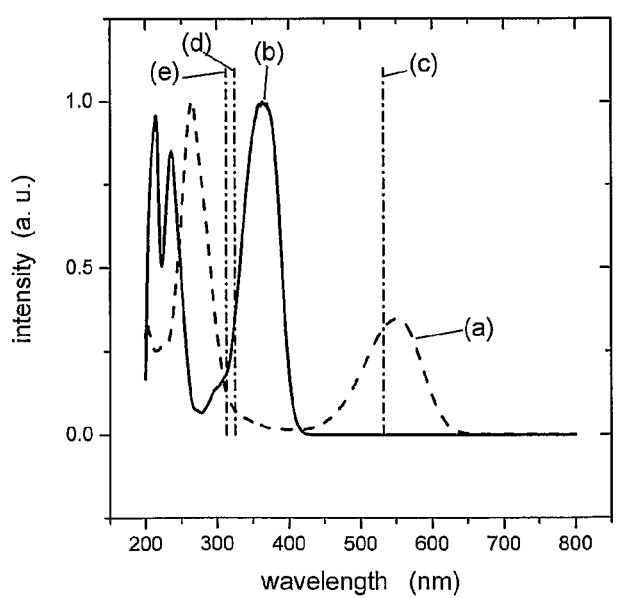
FIG. 17: Absorption spectra of Nile Red (a) and Coumarin 450 (b); For illustration, also the laser wavelengths used for excitation of the two dyes are shown: Nd:YAG at 532 nm (c), HeCd laser at 325 nm (d), and Nd:YAG pumped parametric oscillator in the range of 313-320 nm (e).

Wavelength-Dependent Cavity Mode Excitation in Fluorescent Polystyrene Beads Through a Thin Silver Film As a direct proof of principle of the different transmittance of thin silver films in the range of the plasma frequency and in the visible regime, respectively, the following experiment was performed. Polystyrene (PS) beads of 10 μm in diameter (Polybead Carboxylate 10.0 micron Polystyrene beads, CAT# 18133, Polysciences, Inc., Warrington, Pa.) were simultaneously doped with two different dyes, one of which with a high excitation efficiency around 320 nm (Coumarin 450, CAS# 26078-25-1, Exciton, Dayton, Ohio), the other one with a high excitation efficiency at 532 nm (Nile Red, CAS# 7385-67-3, Lambda Fluoreszenz-techno-logie GmbH, Graz, Austria). The absorption spectra of the two dyes are displayed in FIG. 17 together with the emission wavelengths of the lasers used. For doping, each 250 μl of saturated xylene (CAT# 46004-70, Kanto Chemicals Co., Inc., Japan) solutions of the two dyes were mixed and then placed on top of 6 ml of deionized water (Millipore MilliQ>18MΩcm), which had been placed before into a 50 ml brown glass vial. 100 μl of the native bead suspension were then introduced into the water sub-phase. The two-phase system was gently stirred, until the xylene became entirely vaporized.

The dye-doped colloidal particles 1 were then placed onto a silver-coated glass cover slip as follows. For formation of the silver film, 80 nm of silver (99.99%, Furuuchi, Kagaku K. K., Japan) were evaporated on a ~0.16 mm glass cover slip (NEO micro cover glass, Matsunami Glass, Ind., Ltd., Japan), which had been cleaned by an ozone treatment (Bioforce Nanosciences, Inc., Ames, Iowa) for 1 hour prior to evaporation. Then, 20 μl of the doped bead suspension were placed onto the slightly tilted substrate 5 and allowed to dry, resulting in a sparse coverage of the silver film with 10 μm PS beads.

Thus prepared samples were studied by means of the optical set-up sketched in FIG. 16, using detection scheme II. For fluorescence excitation, the Nd:YAG laser was utilized and operated either at 313 nm or 532 nm, respectively. For detection, the Triax 550 monochromator and the iDUS CCD camera were applied. The monochromator was mainly used with the 600 L/mm grating and an entrance slit opening of 100 μm.

Figure 18:
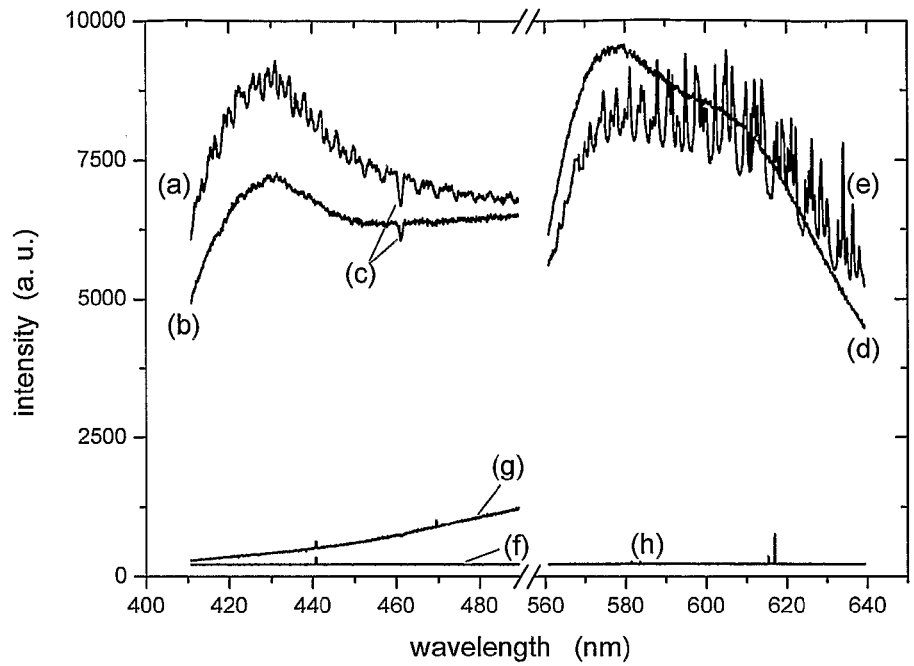
FIG. 18: Whispering gallery mode excitation in Coumarin 450 and Nile Red-doped polystyrene beads by means of 313 nm and 532 nm excitation, respectively.

The experiment is designed such to demonstrate the different transmittance of a thin silver film for UV and visible light, respectively. The fluorescence emission from silver-coated beads is also heavily influenced by the differences in the reflectance of the silver shell in the two emission wavelength ranges of the dyes. Therefore, the dye-doped PS beads remain uncoated, thereby leaving any differences in the fluorescence emission of the bead to differences in the transmittance of the silver film. For reference, beads were also placed onto an uncoated glass cover slip. Such a reference experiment is important for two reasons. First of all, it allows to demonstrate that whispering gallery modes (WGM) can be excited in surface-adsorbed PS beads and detected with the set-up depicted in FIG. 16. Secondly, as will be shown below, the excitation intensities required to achieve a fluorescence intensity of the same order from a bead excited either with UV or visible laser radiation are quite different. These differences are caused by differences in the dye-uptake of the beads by above described inking procedure and different excitation efficiencies of the dyes, by the chromatic aberration of the silica lens, by a partial absorption of the UV light in the cover slip, and by differences in the grating efficiency and CCD sensitivity in the two different emission wavelength ranges of the dyes. Further, minor chromatic aberrations of microscope and fiber coupling optics might come into play. To account for all these differences in an appropriate fashion, the excitation intensities of the two laser wavelengths (313 nm and 532 nm) were adjusted such that a similar fluorescence intensity was monitored by the CCD camera, when the reference sample was studied in the two emission wavelength ranges of the dyes. The result of this adjustment is displayed in FIG. 18. Shown is the raw data of spectra acquired from an uncoated Coumarin 450 and Nile Red-doped PS bead of about 10 μm in diameter. Spectra (a, b, f, g) were acquired with UV excitation of 313 nm at 1.4 mW laser intensity, spectra (d, e, h) with 532 nm excitation of 0.004 mW. It should be noted that both beams were guided through the same pinhole (~2 mm diameter) placed in front of the 100 mm silica lens (b) to assure the same effective beam diameter. Spectra (a) and (e) were obtained from a spherical particle 1. The excitation of WGM in both cases is clearly observable. The higher relative intensity of the modes around 600 nm can be explained by the higher concentration of the Nile Red inside of the particle 1 which promotes stimulated emission and thus a higher population of the cavity modes. Spectra (b) and (d), in contrast, were obtained from an odd-shaped particle 1 that suffered deformation from spherical shape during the inking process due to overexposure to xylene. WGM are not discernible and the spectra simply reflect the fluorescence emission profile of the two dyes. Since the uncorrected raw data is displayed in FIG. 18 (except for removal of a few cosmic rays that appear occasionally in the spectra acquired with a CCD), the fluctuations in the pixel-to-pixel sensitivity of the CCD can be observed. As one example, an area of reduced sensitivity on the chip is indicated in the spectra by the mark (c). Spectra (f) and (h) are background measurements with the lasers turned off. Here, some stray light from the ceiling lighting can be observed. Spectrum (g) finally was collected with the UV laser turned on but with the laser spot not focused onto a PS bead. Thus, the spectrum resembles the emission characteristics of the glass cover slip due to absorbance of UV light. Obviously, this background adds to the spectrum (b), which otherwise would have a similar line profile as spectrum (d).

Summarizing, the reference experiment yields two results. First of all, WGM can be excited in surface-adsorbed PS beads by UV and visible radiation, respectively, after inking of the PS beads with Coumarin 450 and Nile Red. Secondly, the differences in the excitation and detection efficiencies of the WGM in the two different wavelength regimes can be accounted for by proper adjustment of the laser intensities. The difference in efficiency amounts to I(313 nm)/(1532 nm)=1.40 mW/0.004 mW=350.

Figure 19:
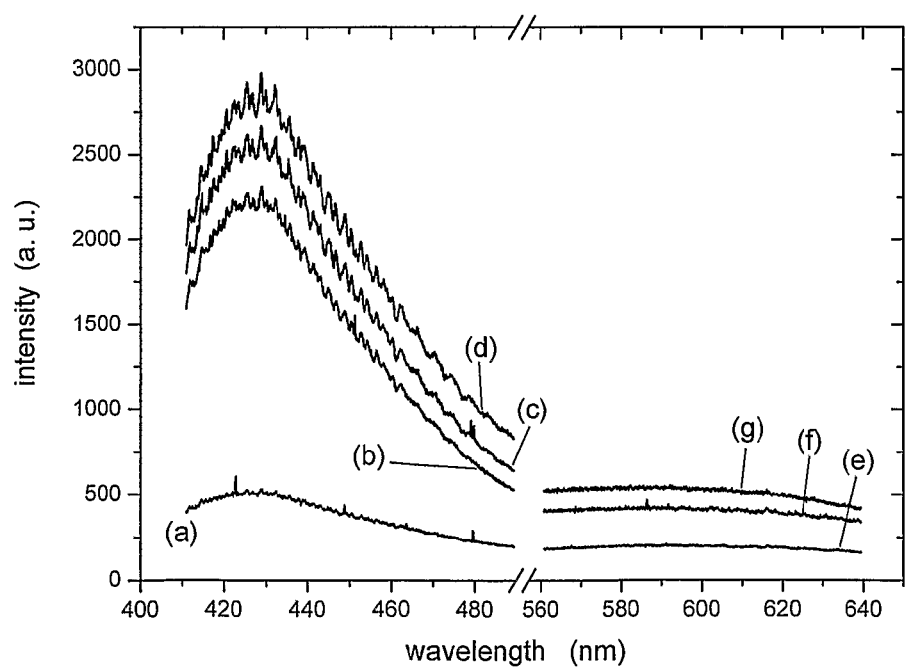
FIG. 19: Whispering gallery mode excitation in Coumarin 450 and Nile Red-doped polystyrene beads by means of 313 nm and 532 nm excitation, respectively, through an 80 nm thick silver film. Due to the high reflection and absorption losses at 532 nm, WGM excitation can be observed only in the case of UV excitation (a-d), where the transmission through the silver film is still significant.

In the next step, a bead deposited on a 80 nm thick silver film on a glass cover slip was studied as depicted in FIG. 16. The entire set-up was used under the same conditions as those used for the reference experiments of FIG. 18. Simply the sample was exchanged, a bead selected and the laser beam slightly re-adjusted to maximize the pump efficiency. Then, the laser intensity was varied and spectra were recorded for each setting. The resulting spectra are displayed in FIG. 19. Spectra (a-d) were acquired with UV excitation at 0.12 mW (a), 0.56 mW (b), 1.05 mW (c), and 1.46 mW (d) laser intensity, respectively. Spectra (e-g) were obtained with 532 nm excitation at 0.01 mW (g), 0.04 mW (f), and 0.06 mW (e) laser intensity, respectively. Note, that in the latter case, the emission intensity does not scale with increasing laser intensity. The intensity ratios $I_{UV}/I_{vis}$ that can be calculated for this set of data range from 0.12 mW/0.06 mW=2 to 1.46 mW/0.01 mW=146, i.e. the ratios are always lower than the ratio of 350 required for equal fluorescence efficiencies via UV and visible excitation, respectively. This means that although excitation with 532 nm excitation is favored in this set of experiments, no WGM excitation can be observed. However, in case of the UV excitation, even at intensities significantly lower than the expectedly required ones, a mode evolution can be observed. Again, the unprocessed raw data is shown. At a UV pump intensity of 1.46 mW, the maximum fluorescence intensity around 430 nm (spectrum (d)) amounts to about 3000 CCD counts, which is 33% that of the intensity found for the reference sample shown in FIG. 18. This attenuation is in excellent agreement with the expected decrease in total transmission of UV radiation through an 80 nm thick silver film as displayed in FIG. 15.

Altogether, the findings presented here do not only illustrate the previously calculated differences in transmittance of thin silver films in the UV and visible regime, respectively, but further demonstrate the feasibility of exciting cavity modes by means of illuminating dye-doped PS beads through an 80 nm thick silver film.

Example 9

Excitation of Cavity Modes in Silver-Coated Fluorescent Polystyrene Beads

In this example the existence of cavity mode inside of dye-doped PS beads fully capsulated into a silver shell is demonstrated.

The same materials and instruments were used as described in Example 8. The optical set-up described in Example 7 was used in both configurations, depending on the sample under study. During the experiments of Example 8 we found that the particles 1 doped with Coumarin 450 and Nile Red show also significant fluorescence around 600 nm when excited with UV radiation despite of the fact that the main emission of the Coumarin 450 is located around 430 nm. We account two reasons for this. According to FIG. 17, Nile Red exhibits slight absorption around 320 nm as well as around 450 nm, i.e. the emission range of the Coumarin 450. Therefore, besides direct excitation by means of the UV radiation, also light emitted from the Coumarin 450 can be re-absorbed by the Nile Red. Both effects cause fluorescence emission in the region around 600 nm. According to this finding, the excitation of cavity modes in Coumarin 450 and Nile-Red-doped PS beads can be studied as a function of the excitation wavelength without any changes of the detection settings, i.e. in the same wavelength range of fluorescence emission. As in Example 8, the excitation intensity of the laser lines has to be adjusted properly to account for differences in the excitation efficiency and to correct for the chromatic aberrations of the lens (b), i.e. to correct the different locations of the focal point for the two wavelengths.

Figure 20:
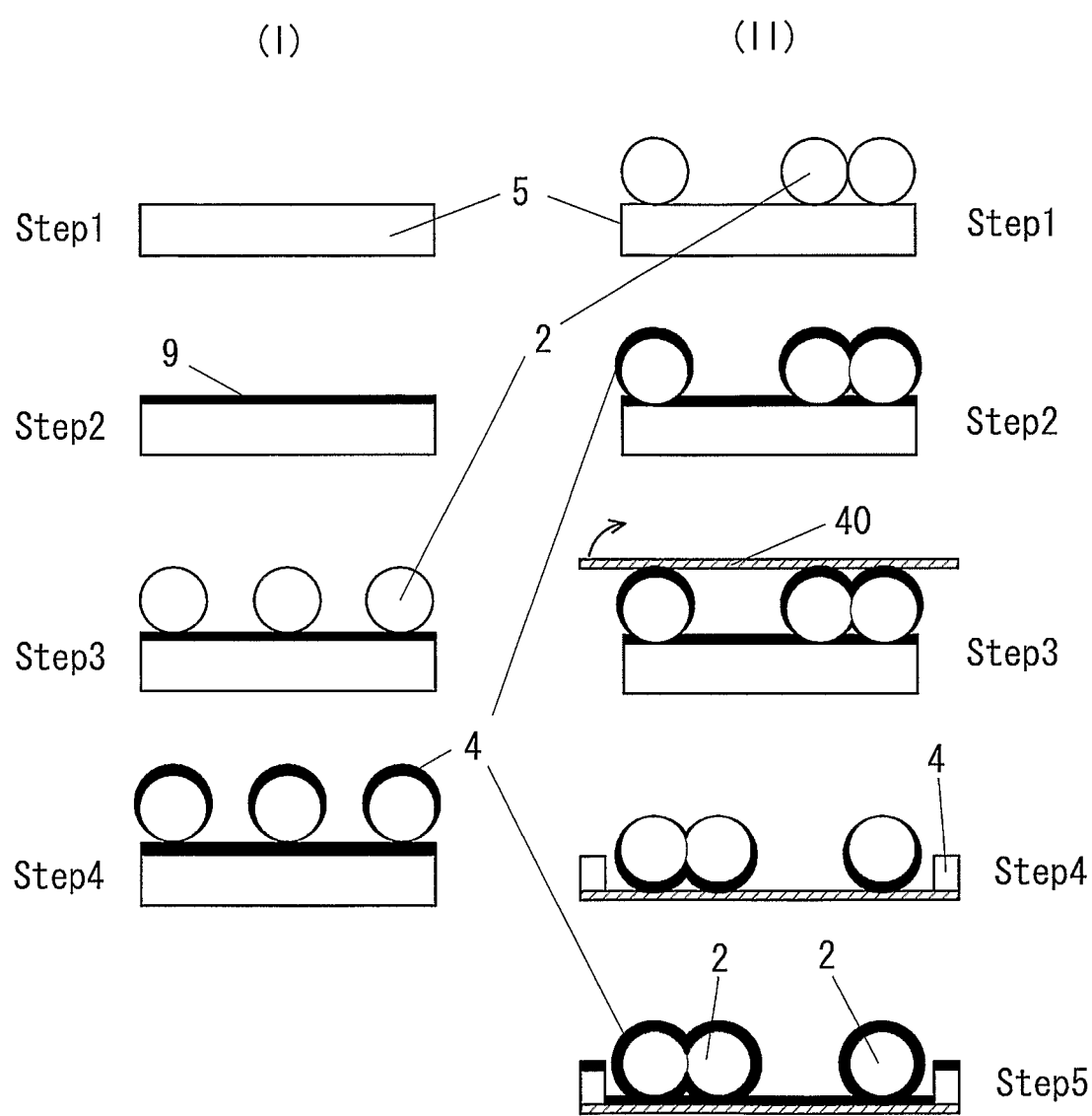
FIG. 20: Fabrication schemes for non-metallic fluorescent particles entirely enclosed in a metal shell of well-defined thickness.

To achieve an enclosure of the PS beads with a silver shell of well defined thickness, the samples prepared in Experiment 7 were additionally coated by evaporating 70 nm of silver at a low vacuum pressure ($2.5 \times 10^{-3}$ mbar pure nitrogen atmosphere) onto that side of the cover slip bearing the PS beads. This procedure assures that the entire free surface area of the beads' surface is coated with the metal due to collisions of the evaporated silver atoms with the residual gas. The coating procedure is illustrated in FIG. 20 as scheme (I) which was also disclosed in the U.S. Provisional Application No. 60/796,162 by the applicant of this application. In this scheme (I), after a substrate 5 is disposed (step 1), a thin film 9 is deposited by means of evaporation or sputtering onto a substrate 5 (step 2). Then, the non-metallic cores 2 are sparsely disposed on the metal film 9 (step 3), e.g. via drop coating from highly diluted suspension. Finally, a second metal layer 4 is deposited via sputtering or low-vacuum evaporation such as to coat the entire free particle surface with a metal layer of well-defined thickness (step 4).

The samples were alternatively excited at 320 nm and 532 nm, respectively, using the pulsed output of the Nd:YAG laser. For detection, the same settings as in Example 8 were applied.

Figure 21:
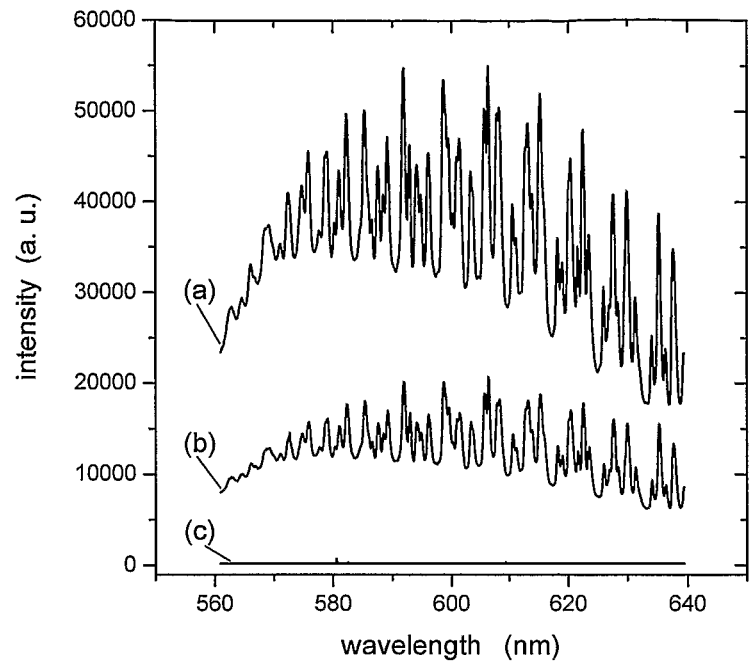
FIG. 21: Whispering gallery mode excitation in a Coumarin 450 and Nile Red-doped polystyrene bead in the emission wavelength range of the Nile red due to excitation with 532 nm (a) and 320 nm (b) radiation, respectively.

FIG. 21 displays a reference experiment. The Coumarin 450 and Nile Red-doped beads prepared for Example 8 were placed onto a fused silica window of 6 mm thickness (CAT# WG 41050, Thorlabs Japan, Inc.) to yield a sparse decoration with PS beads after drying of the suspension. Due to the high thickness of the substrate 5, the optical set-up was utilized in detection scheme (I) of FIG. 16. Since the absorption of silica above 300 nm is basically negligible, a much lower excitation intensity was required for UV excitation of WGM at 320 nm as compared to the experiments involving glass cover slips. We used 0.04 mW to obtain spectrum (b) of FIG. 21. Spectrum (a) was acquired with 532 nm radiation at 0.02 mW. Spectrum (c) finally was achieved under the same conditions as spectrum (b), however without any bead. Since the silica does not absorb UV light, no white light fluorescence is generated as is the case of the glass cover slips. Therefore, the baseline of the spectra is now basically zero, i.e. simply resembles the dark noise of the CCD camera. One small peak above 580 nm can be assigned to a neon line of the sealing light. Except for the difference in absolute intensity, both spectra obtained from the PS bead show the identical resonance features. This stresses the fact that cavity modes are basically a physical property of the cavity and thus independent from the way of their excitation. Slight changes in the linewidths of the modes, however, might arise from differences in the stimulated emission of the dye if pumped at the two different wavelengths.

Altogether, the reference experiment demonstrates the excitability of WGM in the regime around 600 nm by means of 320 nm and 532 nm radiation, respectively. Further, it proves that the modes observed are not due to interference inside of the substrate 5.

Figure 22:
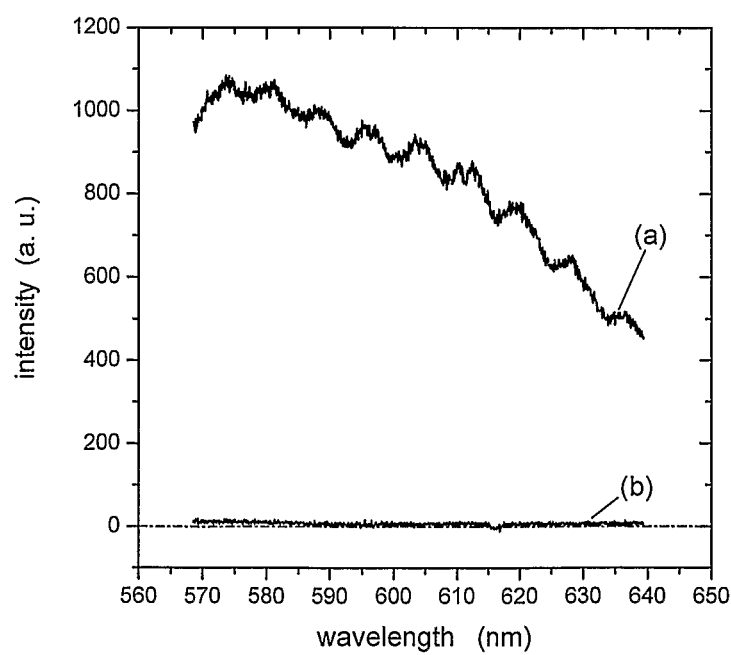
FIG. 22: Cavity mode excitation of dye-inked polystyrene beads enclosed into a silver shell of 70 nm thickness; (a) excitation with 320 nm radiation; (b) excitation with 532 nm excitation.

FIG. 22 displays the spectra obtained from a Coumarin 450 and Nile Red-doped PS bead encapsulated by a 70 nm thick silver shell fabricated by low vacuum thermal evaporation as described above. This time, a glass cover slip was used together with detection scheme (I) as already utilized in Example 8. Therefore, the same energy scale can be applied. We used 2.20 mW intensity for the 320 nm beam and 0.15 mW intensity for 532 nm excitation. Thus the intensity ratio is about 15. Spectrum (a) of FIG. 22 was acquired by means of 320 nm excitation. Clearly, a mode spectrum can be observed. In contrast, excitation with 532 nm radiation does not yield any signal at all due to the high reflectance of the metal coating 4 in this regime. The two spectra are baseline-corrected, i.e. a measurement taken under the same conditions, however, with the laser turned off was subtracted from the two spectra. Thereby it becomes obvious that the silver-coated PS bead does hardly show any fluorescence emission when illuminated with the 532 nm radiation.

Therefore, altogether, the experiment does not only prove the existence of cavity modes in silver-coated particles 1, but further gives another example of the switching behavior of the silver shell.

Example 10

Cavity Mode Excitations in Clusters of Particles

In this example the existence of cavity mode inside of a cluster consisting of three dye-doped PS beads fully capsulated into a silver shell is demonstrated.

The same materials are used as in Example 8. This time, however, the PS beads of 3 μm and 10 μm nominal diameter, respectively, were doped only with Coumarin 450 to avoid competition with the Nile Red and thus to optimize excitability of the beads around 450 nm. The beads were then drop-coated on an ozone-cleaned glass cover slip as before, yielding sparse coverage. For formation of the silver shell, 50 nm of silver (99.99%, Furuuchi, Kagaku K. K., Japan) were evaporated at a low vacuum pressure ($5 \times 10^{-4}$ mbar) onto that side of the cover slip bearing the PS beads. As already explained above, this procedure assures that the entire free surface area of the beads' surface is coated with the metal. The coating procedure is illustrated in FIG. 20 as scheme (II) which was also disclosed in the U.S. Provisional Application No. 60/796,162. In this scheme (II), the substrate 5 is decorated with a sparse layer of non-metallic particles 2 (step 1), then a first metal deposition 4 is performed, which coats the entire free surface of the particles 2, e.g. by sputtering or low-vacuum evaporation (step 2); an adhesive tape 40 (Kokuyo, Japan) is fixed on top of the metal-coated particles 2 (step 3); the adhesive tape 40 is pulled off and fixed to a rectangular frame 41 from below (step 4), thereby exposing that part of the particle surface formerly in contact with substrate 5; finally another metal deposition 4 of same type as the first one is performed to yield entirely and homogeneously metal-coated particles (step 5). The rectangular frame 41 can be made from the lid of a polystyrene cell culture dish (CAT# 430165, Corning) and the low vacuum evaporation of 50 nm of silver was repeated through the aperture of the PS frame. By means of this procedure, entirely closed metallic cavities of well-defined thickness can be fabricated according to scheme (c) of FIG. 5, i.e. single particles are entirely encapsulated, while clusters of particles form non-coated contacts to each other but not to the substrate. According to this procedure, entirely closed metallic cavities of well-defined thickness can be fabricated.

Figure 23:
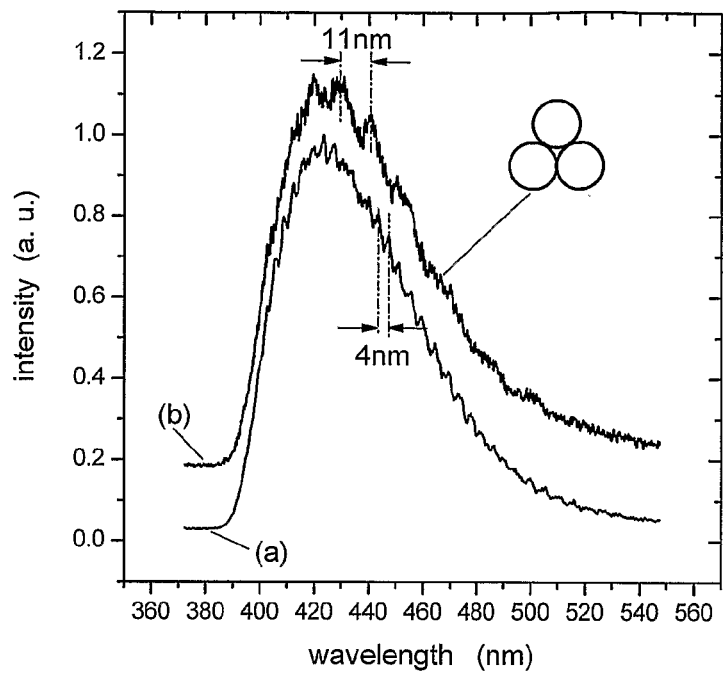
FIG. 23: Cavity mode excitation in a Coumarin 450 and Nile Red-doped polystyrene bead enclosed in a 50 nm thick silver coating; (a) single bead with a nominal diameter of 10 μm; (b) cluster consisting of three beads with a nominal diameter of 3 μm, respectively.

The samples were then studied by means of the detection scheme (II) of FIG. 16. This time, the cw-HeCd laser operated at 325 nm and 0.02 mW intensity was used for excitation, while the detection system consisted of the SP-2500 equipped with the PI-MAX:512 CCD camera. The 150 L/mm grating was chosen and the width of the entrance slit set to 12 μm. Integration time was typically about 60 s. FIG. 23 displays the fluorescence emission from a single bead of 10 μm nominal diameter (a) as well as a trimer consisting of 3 μm beads arranged in triangular configuration (b). The presence of cavity modes in both spectra can be clearly observed as undulation in the fluorescence emission from the peaks. Accordingly, this experiment exemplifies the existence of cavity modes in more complex systems than single spherical beads, which may allow the construction of more complex sensors such as those sketched in FIGS. 5, 8, and 9.

Example 11

Sensing Using Cavity Modes of Silver-Coated Fluorescent Polystyrene Beads

In this example it is demonstrated that fluorescent non-material particles 2 encapsulated in a metallic coating 4 can be used for optical sensing. As in the previous example, the fluorescence emission is chosen such that it falls into the regime of the surface plasmon resonance excitation of the metal shell.

Figure 24:
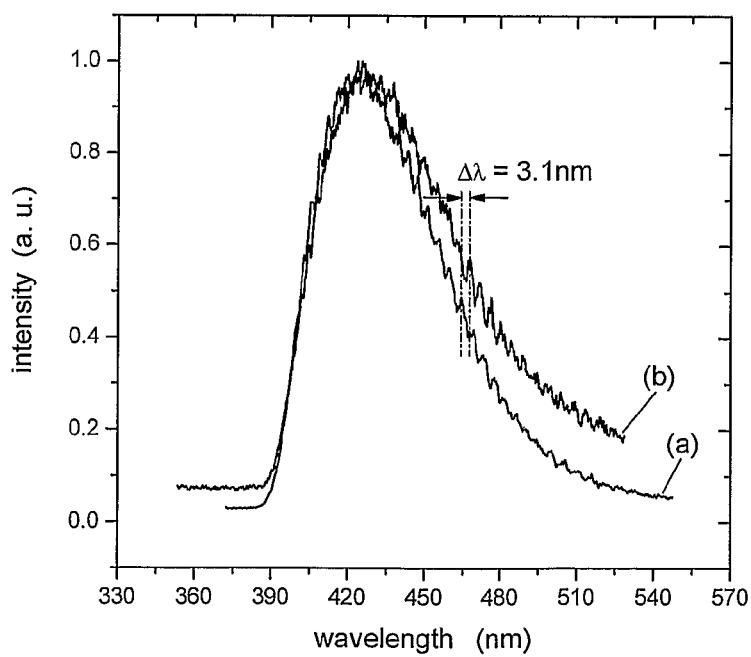
FIG. 24: Cavity mode excitation in a Coumarin 450-doped polystyrene bead enclosed in a 50 nm thick silver coating in the region of the silver surface plasmon resonance. The bead has a nominal diameter of 10 μm, the two spectra were recorded prior to (a) and after (b) adsorption of a monolayer of hexadecanethiol on the silver shell, which causes a shift in the cavity mode positions of about 3 nm.
Figure 25:
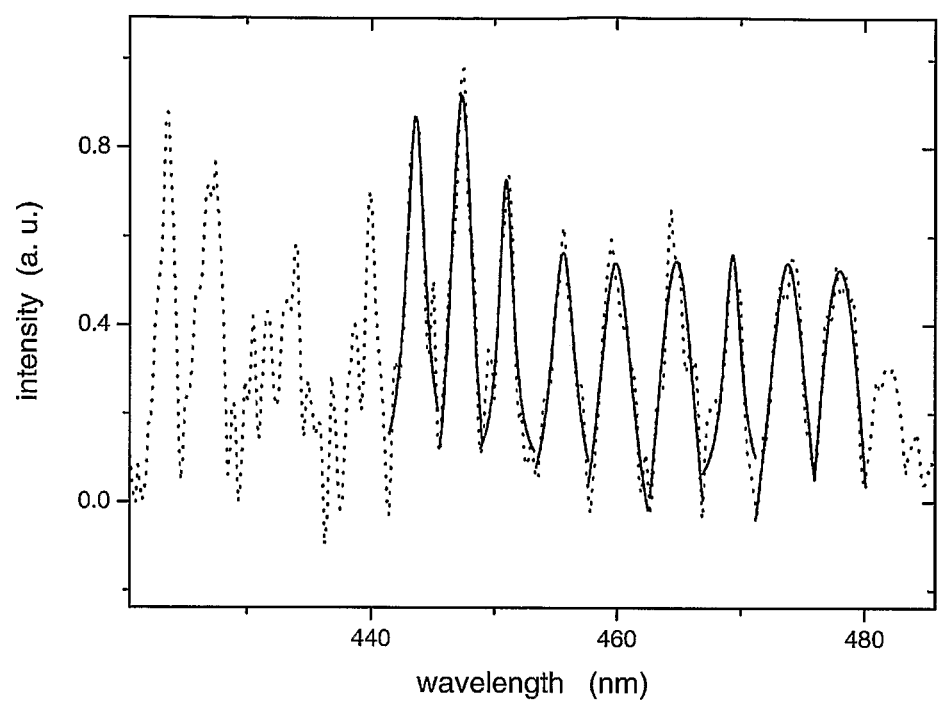
FIG. 25: Close-up of spectrum (a) of FIG. 24 after baseline substraction. The data is represented by the dotted line. The solid lines are fits to the individual cavity mode resonances by means of Lorentz profiles. The resulting peak positions, linewidths, and quality factors of the modes are given in Table 3.

The surface plasmon resonance of a thin silver film in contact with air is located around $\lambda_{SP}=\sqrt{2}\lambda_P=\sqrt{2}320$ nm=450 nm, where $\lambda_p$ is the wavelength of the plasmon resonance of bulk silver as discussed in previous examples. Thus, the Coumarin 450 doped particles 1 used in the previous example emit in the range of surface plasmon excitations of thin silver films. To prove whether cavity modes in this range can be used for optical sensing, we adsorbed a monolayer of hexadecanethiol (HDT) from ethanolic solution onto the single 10 μm particle 1 already shown in FIG. 23. The two spectra obtained from the particle 1 before (a) and after (b) of two hours of immersion into 500 μM HDT solution is displayed in FIG. 24. While the lineshape of the spectrum after adsorption resembles the one prior to adsorption very nicely, a clear shift of about 3 nm in the resonance positions of the cavity modes can be observed. Although the nominal size of the bead used in this study is smaller than the practical resolution limit of standard surface plasmon resonance imaging (~25 μm², see e.g. J. M. Brockman et al., Annu. Rev. Phys. Chem. Vol. 51, pp. 41-63, 2000), the shift we achieve here is of the same order. This demonstrates not only that the core-shell particles 1 described in the present patent application can be applied to optical sensing, but exemplifies further that they may provide an interesting alternative to state-of-the-art optical biosensors based on surface plasmon resonance in terms of sensitivity and lateral resolution. FIG. 25 illustrates close-up of spectrum (a) of FIG. 24 after baseline substraction. The data is represented by the dotted line. The solid lines are fits to the individual cavity mode resonances by means of Lorentz profiles. The resulting peak positions, linewidths, and quality factors of the modes are given in Table 3.

Example 12

Determination of Cavity Mode Q-Factors of Silver-Coated Fluorescent Polystyrene Beads In this example the Q-factors achievable with a dye-doped polystyrene bead coated with a silver shell of 50 nm thickness are determined. We use the spectrum (a) of FIG. 24 for this purpose, which was obtained from a Coumarin 450-doped PS bead encapsulated into a 50 nm thick silver shell by means of scheme (II) of FIG. 20. An SEM image of a corresponding particle found on the same sample is shown in FIG. 25.

To allow a simple determination of the bandwidths of the cavity modes, the spectrum is first background corrected, i.e. the spontaneous fluorescence emission, which dominates the entire spectrum, is subtracted (using the baseline tool of OriginPro 7.5 SR4, OriginLab Corp., Northampton, Mass.). A close-up of the corrected spectrum is displayed in FIG. 25. In the next step, Lorentz profiles are fitted to the individual resonances by first restricting the fitting range to the two adjacent minima of a single peak and then performing the fit (OriginPro 7.5 SR4). In FIG. 25, the background corrected spectrum is shown as dotted line, while the individual fit results are displayed as solid lines. The agreement between data and fits is reasonable in particular with respect to the linewidths of the resonances, which is most important here.

Table 3 shows the peak positions, linewidths, and the resulting Q-factors calculated according to eq. 1 of the evaluated peaks. The Q-factors range from about 50 to 300 with an average of 170±87. In above calculations (Examples 2 and 3) all estimations were made assuming a Q-factor of 100. Therefore, our experimental results demonstrate that the Q-factors achievable in the visible regime with silver shells still sufficiently transparent around 320 nm to allow for cavity mode excitation, are even higher than required for the validation of the theoretical predictions.

TABLE 3

|  | Position (nm) | | | | | | | | |
| --- | --- | --- | --- | --- | --- | --- | --- | --- | --- |
|  | 443.6 | 447.3 | 451 | 455.6 | 459.9 | 464.8 | 469.3 | 473.8 | 478 |
| Linewidth (nm) | 1.93 | 2.53 | 1.47 | 2.53 | 3.8 | 5.24 | 1.71 | 4.73 | 8.64 |
| Q-factor | 229.8 | 176.8 | 306.8 | 180.1 | 121.0 | 88.7 | 274.4 | 100.2 | 55.3 |

Example 13

SEM Images

Finally, SEM images of particle(s) 1 are shown in FIGS. 26 to 29.

Figure 26:
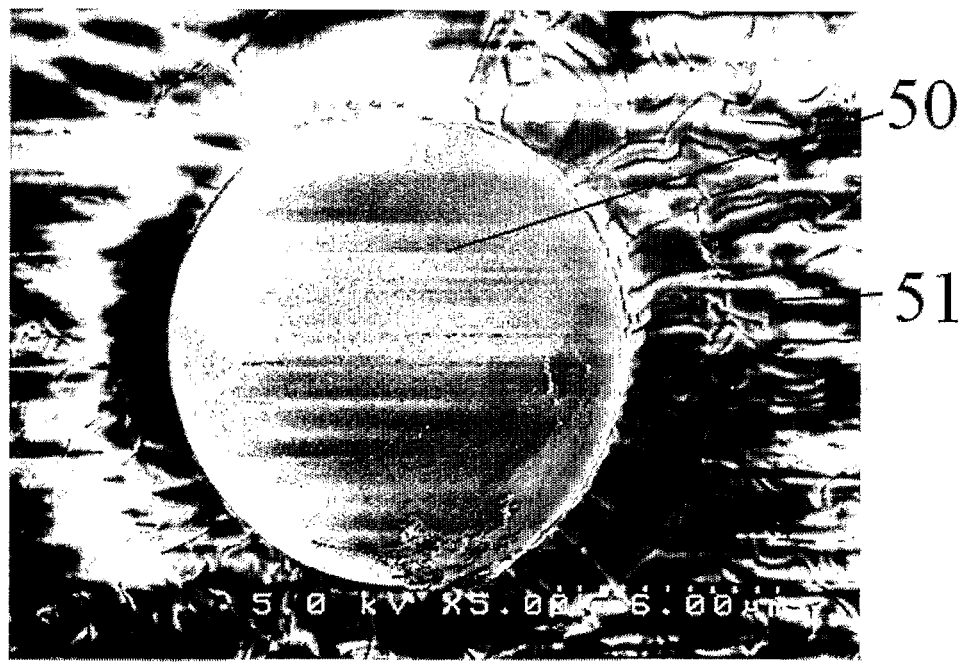
FIG. 26: Scanning electron microscopy (SEM) image of a particle of the sample used in Example 11.

FIG. 26 shows SEM image of a particle of the sample used in Example 11. A reference number 50 denotes coumarin 450-doped PS bead entirely coated with a 50 nm thick silver shell according to the procedure illustrated in FIG. 20(II); a reference number 51 denotes silver deposited on the adhesive tape according to FIG. 20(II).

Figure 27:
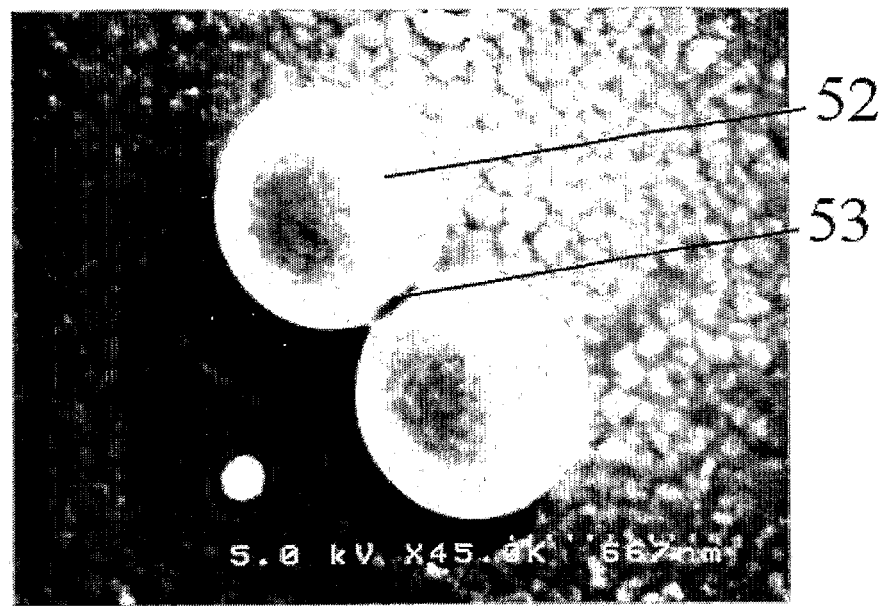
FIG. 27: SEM images of clusters of silver-coated particles fabricated according to scheme (d) of FIG. 5.

FIG. 27 shows SEM images of clusters of silver-coated particles fabricated according to scheme (d) of FIG. 5. a reference number 52 denotes dimer of two Coumarin 450-doped PS particles with a nominal diameter of 750 nm coated with a 50 nm thick silver shell by low vacuum evaporation ($5\times10^{-4}$ mbar nitrogen atmosphere); the formation of a silver bridge 53 connecting the two particles is clearly discernible.

Figure 28:
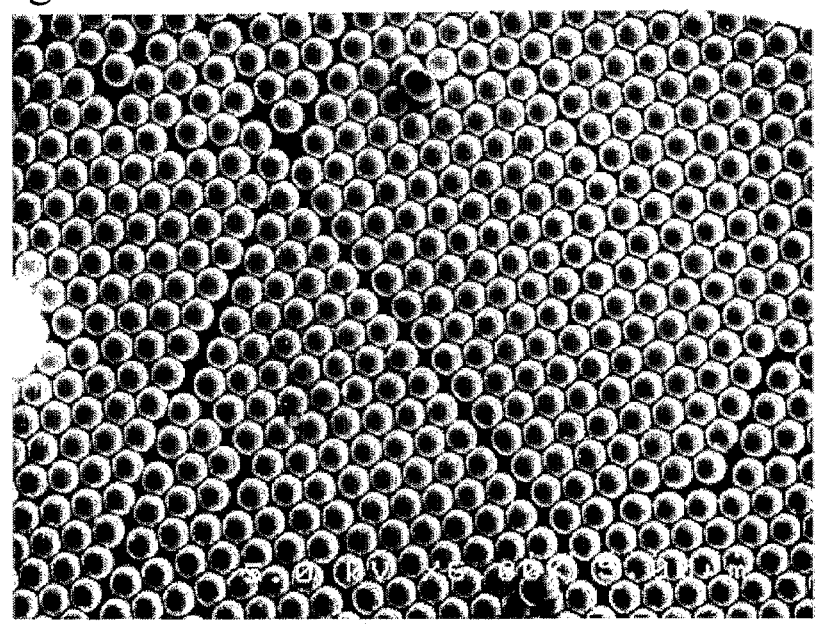
FIG. 28: SEM images of clusters of silver-coated particles fabricated according to scheme (d) of FIG. 5.

FIG. 28: SEM images of clusters of silver-coated particles fabricated according to scheme (d) of FIG. 5. Hexagonally dense-packed cluster of silver-coated Coumarin 450-doped 750 nm PS beads to exemplify the potential of the method to form metal-coated photonic crystals of fluorescent non-metallic particles.

Figure 29:
FIG. 29: SEM images of clusters of silver-coated Coumarin 450-doped PS beads of 750 nm in diameter after lift-off of some of the particles from the surface.

FIG. 29: SEM images of clusters of silver-coated Coumarin 450-doped PS beads of 750 nm in diameter after lift-off of some of the particles from the surface. 50 nm of silver had been deposited onto the surface-immobilized beads at low vacuum conditions ($5\times10^{-4}$ mbar nitrogen atmosphere). The positions of the removed beads can still be seen from the arrangement of silver clusters on the surface of the substrate, which had formed during evaporation through the formerly present interstices between the particles. The remaining particles show clearly the silver coating 54 and the contact points 55 with the formerly present particles. The silver coating forms semicircular apertures at the former contact points 55. Circular silver apertures can also be observed on the substrate surface around the former contact points of the beads with the substrate 56. The apertures 55 and 56 both have diameters of about 190 nm and thus are examples of small apertures which allow for tunneling of photons. In particular, they fulfill the condition $A_{ph} < \pi/4\lambda^2$, where $A_{ph}$ is the area of the aperture and $\lambda$ is an optical wavelength above 190 nm.

Heretofore, the present invention is explained with reference to the embodiments. However, various changes or improvements can be applied to the embodiments.

What is claimed is:

1. A particle comprising:
   a non-metallic core having a fluorescent material; and
   a metallic shell homogenously encapsulating the non-metallic core;
   wherein the metallic shell has transparency for an electromagnetic radiation having a first range of wavelengths to excite the fluorescent material and reflectance for at least a part of an electromagnetic radiation having a second range of wavelengths emitted by the fluorescent material to confine the electromagnetic radiation having the said part of the second range of wavelengths in the metallic shell and thereby at least one cavity mode with a Q factor of greater than about 50 is excited; where the Q factor is calculated from position and line width of the cavity mode.

2. The particle as set forth in claim 1, wherein the non-metallic core has fluorescent material selected from the group consisting of dye molecules, quantum dots, carbon nanotubes, Raman emitters.

3. The particle as set forth in claim 1, wherein the fluorescent material is either contained in the core or adsorbed on the core surface.

4. The particle as set forth in claim 1, wherein at least one part of the emission wavelength range of the fluorescent material, when irradiated at $\lambda_{exc}$, covers the spectral position of the surface plasmon resonance of the metallic shell.

5. The particle as set forth in claim 1, wherein the fluorescent material is excited by means of ultrashort laser pulses, so that the population of the excited states exceeds that of the ground state at least temporally, that is a basic lasing condition is fulfilled.

6. The particle as set forth in claim 1, wherein the volume of the cavity core (V), its refractive index ($n_{cav}$), its quality factor (Q), and the emission wavelength ($\lambda_{em}$) of the fluorescent material are chosen so as to satisfy the inequality (I):

$$1 < 3Q\left(\frac{\lambda_{em}}{n_{cav}}\right)^3 / 4\pi V. \tag{I}$$

7. The particle as set forth in claim 1, wherein the cavity volume ($V_{min}$), the refractive index of the cavity ($n_{cav}$) and at least one of the emission wavelength ranges ($\lambda_{em}$) of the fluorescent material inside the core are selected so as to satisfy the condition (II):

$$V_{min} = f\left(\frac{\lambda_{em}}{n_{cav}}\right)^3, \quad (II)$$

and the factor f is <100.

8. The particle as set forth in claim 7, the factor f is <10.

9. The particle as set forth in claim 8, the factor f is <1.

10. The particle as set forth in claim 1, wherein at least one of the emission regimes ($\lambda_{em}$) of the fluorescent material, the cavity volume V, its refractive index $n_{cav}$ and its Q-factor are selected so as to hold the following condition:

$$\frac{\lambda_{em} d^2 Q^2}{n_{cav}^2 V} > \frac{\pi c \varepsilon_0 \hbar}{2} = 4.40 \times 10^{-37} \ Coulomb^2, \quad (III)$$

where $\lambda_{em}$ is the vacuum emission wavelength of the fluorescent material and d is the transition dipole moment of the fluorescent material corresponding to $\lambda_{em}$.

11. The particle as set forth in claim 1, the metallic shell consists of silver.

12. The particle as set forth in claim 11, the metallic shell consists of silver having thicknesses between 10 and 70 nm.

13. The particle as set forth in claim 12, the metallic shell consists of silver having thicknesses between 50 and 70 nm.

14. A coupled particle system containing at least two of the particles according to claim 1, wherein the particles are located in close contact with each other such that cavity mode within the metallic shells couple with each other.

15. The coupled particle system as set forth in claim 14, wherein the particles are located in close contact with each other such that photons can tunnel from one cavity to a neighboring one with a probability >10$^{-6}$.

16. The coupled particle system as set forth in claim 14, wherein the particles are located in close contact with each other such that the cavity modes of the cavities show a mode splitting due to the contact.

17. The coupled particle system as set forth in claim 14, wherein the fluorescent material is excited by means of ultrashort laser pulses, so that the population of the excited states exceeds that of the ground state at least temporally, that is a basic lasing condition is fulfilled.

18. A biosensor for sensing a target molecule, comprising:
the particle according to claim 1;
a capturing molecule that is immobilized on an outer surface of the particle and is capable of capturing the target molecule;
a means for emitting electromagnetic radiation having the first range of wavelengths; and
a detector for detecting electromagnetic radiation having a wavelength around the second range of wavelengths,
wherein the change in the electromagnetic radiation from the particle indicates the capture of the target molecule.

19. The biosensor for sensing a target molecule as set forth in claim 18, wherein the fluorescent material is excited via means of an external electromagnetic radiation, and the detection is performed by means of an optical system, preferably via a fiber probe or waveguide.

20. A biosensor for sensing a target molecule as set forth in claim 19, wherein a source of the external electromagnetic radiation is a laser beam.

21. A biosensor for sensing a target molecule as set forth in claim 20, wherein a source of the external electromagnetic radiation is an ultrashort pulse laser beam.

22. Arrays or clusters of particles of the particles described in claim 1.

23. A free floating particles system, wherein the particles have a structure described in claim 1 and are dispersed in a fluid that is transparent to the electromagnetic radiations having a first range of wavelengths which excite the fluorescent material and the electromagnetic radiation having a second range of wavelengths emitted by the fluorescent material.

24. A single substrate-supported particles system, wherein the particles have a structure described in claim 1 and are partially or entirely buried into the substrate that is transparent to the electromagnetic radiations having a first range of wavelengths which excite the fluorescent material and the electromagnetic radiation having a second range of wavelengths emitted by the fluorescent material.

* * * * *